(12) United States Patent
Katz

(10) Patent No.: US 12,409,239 B2
(45) Date of Patent: Sep. 9, 2025

(54) PARTICLES FOR USE IN HYPERPOLARIZATION

(71) Applicant: BEACON MRI LTD, Zichron Yaacov (IL)

(72) Inventor: Itai Katz, Nofit (IL)

(73) Assignee: BEACON MRI LTD, Zichron Yaacov (IL)

( * ) Notice: Subject to any disclaimer, the term of this patent is extended or adjusted under 35 U.S.C. 154(b) by 0 days.

(21) Appl. No.: 17/847,194

(22) Filed: Jun. 23, 2022

(65) Prior Publication Data

US 2022/0409748 A1 Dec. 29, 2022

Related U.S. Application Data

(60) Provisional application No. 63/215,125, filed on Jun. 25, 2021.

(51) Int. Cl.
*A61K 49/18* (2006.01)

(52) U.S. Cl.
CPC .............................. *A61K 49/1818* (2013.01)

(58) Field of Classification Search
CPC ..... A61K 49/08; A61K 49/1818; C09C 1/021
See application file for complete search history.

(56) References Cited

U.S. PATENT DOCUMENTS

| | | | |
|---|---|---|---|
| 7,474,095 B2 | 1/2009 | Levitt | |
| 8,980,225 B2 | 3/2015 | Warren | |
| 9,623,126 B2 | 4/2017 | Weissleder | |
| 10,649,044 B2 | 5/2020 | Jelezko | |
| 10,722,596 B2 | 7/2020 | Pokroy | |
| 2005/0136002 A1 | 6/2005 | Fossheim | |
| 2007/0063700 A1 | 3/2007 | Levitt | |
| 2007/0166232 A1 | 7/2007 | Cho | |
| 2007/0258907 A1 | 11/2007 | Davis | |
| 2008/0284429 A1 | 11/2008 | Marcus | |
| 2009/0016964 A1 | 1/2009 | Kalechofsky | |
| 2009/0191131 A1 | 7/2009 | Fossheim | |
| 2010/0092390 A1 | 4/2010 | Marcus | |
| 2011/0195028 A1 | 8/2011 | Warren | |
| 2016/0101196 A1 | 4/2016 | Medina | |
| 2016/0306020 A1 | 10/2016 | Jannin | |
| 2019/0257904 A1 | 8/2019 | Zheng | |
| 2020/0191735 A1* | 6/2020 | Negoro | G01N 24/12 |
| 2022/0018915 A1* | 1/2022 | Schwartz | G01N 24/08 |

FOREIGN PATENT DOCUMENTS

| | | | |
|---|---|---|---|
| KR | 2018/0091733 | 8/2018 | |
| WO | WO-9935508 A1 * | 7/1999 | ............. A61K 49/08 |
| WO | 2007082048 | 7/2007 | |
| WO | 2007136439 | 11/2007 | |
| WO | 2010042476 | 4/2010 | |
| WO | 2020104854 | 5/2020 | |

OTHER PUBLICATIONS

Uskokovic, Phys. Chem. Chem. Phys., 2020, 22, p. 5531. (Year: 2020).*
Yang et al., Nano Research, 2015, 8(3), p. 751-764. (Year: 2015).*
Sodium bicarbonate, Feb. 19, 2019, https://web.archive.org/web/20190219104257/https://en.wikipedia.org/wiki/Sodium_bicarbonate. (Year: 2019).*
Goehring, Lucas, and Carl A. Michal. "Nuclear spin polarization transfer across an organic-semiconductor interface." The Journal of chemical physics 119.19 (2003): 10325-10329.
Capozzi et al., "Efficient Hyperpolarization of U-13C-Glucose Using Narrow-Line UV-Generated Labile Free Radicals," Angew. Chem. Int. Ed. 2019, 58, 1334-1339.

* cited by examiner

*Primary Examiner* — Michael G. Hartley
*Assistant Examiner* — Leah H Schlientz
(74) *Attorney, Agent, or Firm* — JMB Davis Ben-David

(57) ABSTRACT

Described herein are particles comprising a crystalline matrix and a dopant, wherein one of the atoms of the matrix is $^{19}F$ and $^{31}P$, or $^{13}C$, $^{15}N$, $^{29}Si$, $^{16}O$, $^{17}O$, $^{23}Na$, $^{39}K$, $^{25}Mg$, $^{40}Ca$, $^{43}Ca$ or deuterium; and the dopant is a compound involved in a biological process in a mammalian organism; and wherein the dopant is present in an amount of between 0.01% and 20% of the plurality of particles, and wherein when the matrix comprises an atom selected from the group of $^{13}C$, $^{15}N$, $^{29}Si$, $^{16}O$, $^{17}O$, $^{23}Na$, $^{39}K$, $^{25}Mg$, $^{40}Ca$, $^{43}Ca$ and deuterium, and the dopant is isotopically enriched.

14 Claims, 10 Drawing Sheets
(9 of 10 Drawing Sheet(s) Filed in Color)

PARTICLES FOR USE IN HYPERPOLARIZATION

CROSS REFERENCE TO RELATED APPLICATIONS

Benefit is claimed to U.S. Provisional Patent Application No. 63/215,125 filed Jun. 25, 2021; the contents of which are incorporated by reference herein in its entirety.

FIELD

Provided herein are probes for hyperpolarization to provide elongated $T_1$ times.

BACKGROUND

In magnetic resonance, hyperpolarization is a technique used to boost the received signal from a sample. Under normal circumstances and in magnetic fields commonly used in magnetic resonance practice (a few teslas), the interaction strength between spin half nuclei and the applied magnetic field corresponds to frequencies in the tens-hundreds of MHz range. According to the formula E=hv, this energy is orders of magnitude smaller than ambient thermal energy and hence, according to Boltzmann statistics, there is only a very slight preference for the nuclei to assume the preferred state with respect to the applied field. As a result, the population of nuclei in the state parallel to the field exceeds that in the antiparallel state only by a few parts per million for most substances. Aside from the small excess of nuclei aligned in the parallel state, most of a sample's nuclei cancel each other out. As a result, 99.999% of a sample acts as ballast that does not give rise to any signal. Only a few millionths of the sample is responsible for the entire signal emanating from the sample.

The general notion of hyperpolarization relates to boosting a signal that can be produced from a sample by way of increasing the difference between parallel and antiparallel populations to percents of a sample, tens of percents of a sample, and sometimes even to the entire sample. This feat can be accomplished by various physical methods. The most prevalent include optical pumping, para-hydrogen, and dynamic nuclear polarization (DNP), which is perhaps the most robust and widely used technique. In DNP, one brings unpaired electrons to within interaction range from the target nuclei. The spins are now subject to interaction both with the external field and with each other. Under this modified interaction, appropriate microwave (MW) irradiation, for example at a frequency corresponding to the difference or sum of the electron and nucleus Larmor frequencies, can induce what is known as zero quantum (ZQ) or double quantum (DQ) transitions, respectively. By saturating these transitions, one may impose the electron population difference on the nuclei population giving rise to 3 orders of magnitude increase in polarization. By applying this technique at low temperatures, where electron polarization approaches unity, an additional gain of 1-3 orders of magnitude can be achieved.

DNP, with some adaptation, has been attempted as an aid to both preclinical and clinical MRI. The slightly modified technique is known as dissolution DNP. In this technique the sample is co-dissolved with free radicals of some sort. These provide the unpaired electrons necessary for the DNP process. The sample is then brought to a cryogenic temperature and MW irradiated under a strong magnetic field. The DNP process usually takes around 1-3 hours to polarize the sample nuclei as best as possible. Once the desired polarization level has been reached, a stream of high pressure and hot solvent flushes the sample out and dissolves it. It emerges from the DNP apparatus polarized and ready for use, whether on an NMR spectrometer, as an injectable MRI aid or otherwise.

The modality of dissolution DNP has been in place for a number of years, and has even spurred a few commercialization attempts, such as the clinically approved DNP hyperpolarizer 'Spinlab', released by GE on 2014. However, despite demonstrating great promise as a valuable tool for research and academia, the hyperpolarizer has not been widely accepted for clinical use.

A reason for the lack of wide acceptance of hyperpolarized probes for clinical use is the relaxation nature of most hyperpolarized probes for MRI. When a probe molecule emerges in a hyperpolarized state from a DNP polarizer, its nuclei are far from their equilibrium state. Naturally, a process of returning to equilibrium begins. This process is known as Spin Lattice relaxation. It is characterized by an exponentially decaying behavior that asymptotically reaches equilibrium value with a characteristic time constant known as $T_1$.

The $T_1$ time constant is highly compound specific, and since it arises from the most immediate environment of the nuclei in the compound it is exceedingly hard to manipulate and control. Unfortunate as it is, $T_1$ values of most viable hyperpolarization probes are very short. Just as an example, $T_1$ of pyruvate/pyruvic acid—the most convenient and widely used metabolic probe, is only about a minute. This means that as a minute elapse from exiting the polarizer, the polarization, which required much effort to obtain, is reduced to 30% of its initial value. The process continues exponentially until only equilibrium polarization remains, eliminating all benefits that may be gained from the hyperpolarization process. In other metabolites, $T_1$ values are much shorter. For example, glucose exhibits $T_1$ of ~10 seconds rendering it completely impractical as a hyperpolarized probe, despite its great potential to report on the multitude of physiological metabolic processes it participates in.

Even pyruvate, with its unusually long $T_1$ is exceedingly hard to wield as a hyperpolarized probe—the timing of signal acquisition must be set in a narrow window that begins when the probe has traveled via the circulation to the location of interest within the patient's body and ends with the decay of the hyperpolarized magnetization. This proves too narrow of a window, without even accounting for the fact that the duration of the voyage through the circulation from the site of injection to location of interest is highly variable between patients and also highly variable for a given patient at different times.

As mentioned, this problem is hard to tackle for there is very little room for manipulation within the molecule itself. However, there are currently two known approaches to lengthen probe hyperpolarization. The first is to replace hydrogen atoms in the probe molecule of interest with deuterium. Deuterium nuclei exhibit a much weaker magnetic strength than protons and are thus less effective in promoting $T_1$ relaxation. This approach has been implemented to various metabolites, including glucose, for example, and deuterated compounds for use as hyperpolarization probes are commercially available. Another related approach focuses on the target nuclei, for example Carbon-13 ($^{13}C$) in the vast majority of cases. It is customary to use $^{13}C$ enriched materials as hyperpolarization probes, for it can increase the available signal by an additional two orders of magnitude with respect to using natural abundance, and the extra-effort is small with respect to the entire hyperpolarization process complexity. However, the $^{13}$C nuclei, being magnetically active are themselves relaxation agents that promote their own relaxation, i.e. they are self-affecting. For this reason, partial enrichment or enrichment at specific positions is often preferred over uniform enrichment.

A third approach, described in U.S. Pat. No. 7,474,095 to Levitt et al. is to use the notion of singlet states as a parking state for magnetic order. When two nuclei of the same type are interacting and reside in a singlet state they behave as a single "spinless" entity, very similar to paired electrons which display no magnetic properties (and as opposed to paramagnetic materials). In such a state, every disturbance exerted by the environment on one spin is exerted in an exactly opposite manner on the other, thus maintaining the overall order of the system despite external noises. However, the long-lived singlet state is not an eigenstate of the molecular spin system in a magnetic field as long as the participating nuclei are not magnetically equivalent. In the vast majority of cases nuclei at different positions within a molecule are not equivalent, displaying typical differences in resonance frequencies of a few KHz's. Under these circumstances the spin system rapidly evolves out of the singlet state. To keep it there, an external RF irradiation is applied with the aim of modifying the form of the Hamiltonian so as to halt the evolution of the singlet state, despite the nonequivalence of the two nuclei forming it. In order to effectively perform its task, the interaction with the applied RF must overwhelm the energetic nonequivalence and this calls for RF powers that correspond to nutation frequencies of a good few tens of KHz's.

A fourth method, described in U.S. Pat. No. 8,980,225 to Warren, is similar to the aforementioned one. In this technique, magnetization is stored in chemically equivalent nuclei, which are forced externally into a singlet state. Owing to their chemical equivalence, the singlet state is an eigenstate of nuclei pair also under magnetic field and in fact under any magnetic disturbance that is applicable in moderate lab conditions. This allows to retain their state without modifying their Hamiltonian with intense RF irradiation as is suggested by Levitt. However, the order stored in a singlet pair of chemically equivalent spins is unobservable, The remedy to that, according to the method is to use materials with a chemical structure such that upon action by enzymes, wetting, or some other event that occurs in the body, the equivalent spins become nonequivalent and under the new Hamiltonian they may evolve to give rise to observable magnetization. The exact manner by which the timing of the chemical transformation inside the body is controlled is not specified.

Described above are 4 approaches to $T_1$ elongation. The first two focus on isotopic substitutions in an attempt to eliminate sources of magnetic noise from the immediate environment of the nuclei of interest. This approach typically results in a few tens of percent of improvement. In the best of cases, it may increase $T_1$ by a factor of 2 or 3. Likewise for partial enrichment of target nuclei. These two approaches are not new, and the current problems encountered in hyperpolarization in a clinical setting persist despite their availability and extensive use (for example the $T_1$ value of 10 seconds in glucose is attributed to the uniformly deuterated analog of the molecule. For the native molecule the situation is much worse).

The third approach relies on locking a long-lived singlet state by virtue of continuous RF irradiation. This approach has been demonstrated to extend $T_1$ values by at least an order of magnitude and beyond. However, in a clinical setting this approach is remotely practical because it requires very high RF powers to be applied to the entire body and for prolonged durations. This will inevitably result in unacceptable heating of the patient. The fourth method is applicable only to a limited set of compounds that satisfy the very limiting requirement of having two chemically equivalent NMR nuclei that are also convertible under physiological conditions to non-equivalent. Most metabolites do not meet this condition and therefore this method is not applicable in a general manner.

KR 2018/0091733 discloses porous and biocompatible silicon nanoparticles which are surface modified with functional groups. The disclosed silicon-based nanoparticles can be used for the preparation of a magnetic resonance imaging (MRI) contrast agent; or as a drug delivery carrier since a therapeutic drug can be supported in micropores and mesopores existing in said particle. Specifically, the disclosed particles may be hyperpolarized using dynamic nuclear polarization techniques.

WO 2007/082048 discloses methods for accelerating the ex vivo induction of nuclear hyperpolarization in imaging agents. The imaging agents are solid state materials that include both non-zero and zero spin nuclei.

US 2007/0166232 discloses magnetic nanoparticles comprising a core represented as $Fe_xM^a_vZ_y$ and a shell of an inner-transition element $M^b$, wherein $M^a$ is an inner-transition element, Z is an element of the group VIa, x is greater or equal to 0, and v, y are positive numbers. The magnetic nanoparticles can be selectively modified by at least one molecule (such as liposome, polymer, aliphatic compound or aromatic compound), or further react with at least one substance having specificity (such as an antibody, protein, peptide, enzyme, carbohydrate, glycoprotein, nucleotide or lipid) to form contrast agents or tracers with specificity. The magnetic nanoparticles can be applicable in imaging, diagnosis, therapy, and biomaterial separation.

US 2007/258907 discloses polymer-coated paramagnetic particles which optionally possess targeting ligands, therapeutic agents, or carrier ligands, and to diagnostic and therapeutic uses of such particles. Specifically, disclosed is a paramagnetic particle coated by a cyclodextrin-containing polymer for use in in vivo monitoring of the biodistribution and pharmacokinetics of novel therapeutic agents non-invasively by MR imaging.

US 2009/0191131 discloses a contrast medium for in vivo imaging, wherein said medium comprising a particulate material comprising a matrix or membrane material and at least one contrast generating species.

WO 2010/042476 discloses a method for the preparation of particles having long spin-lattice relaxation times, $T_1$. Examples of materials that may potentially exhibit long-$T_1$ relaxation times include, but are not limited to, silicon-based compounds, e.g., silicon dioxide, silicon nitride, and silicon carbide, carbon, and carbon-based compounds. These particles can be used for various applications in the field of nuclear magnetic resonance, e.g., magnetic resonance imaging (MRI).

SUMMARY

Described herein are particles comprising a crystalline matrix and a dopant, wherein one of the atoms of the matrix is $^{19}$F and $^{31}$P, or $^{13}$C, $^{15}$N, $^{29}$Si, $^{16}$O, $^{17}$O, $^{23}$Na, $^{39}$K, $^{25}$Mg, $^{40}$Ca, $^{43}$Ca or deuterium; and the dopant is a compound involved in a biological process in a mammalian organism selected from the group consisting of: an amino acid, a monosaccharide, a disaccharide, a choline, a nucleobase, a carboxylic acid, or a biological waste product, a metabolite, a neurotransmitter, a peptide, a vitamin, a pharmaceutical agent, a hormone, a psychoactive agent, an alcohol, a glycol, glycerine, a fatty acid, a phospholipid, a lecithin, or cholesterol; and wherein the dopant is present in an amount of between 0.01% and 20% of the plurality of particles, and wherein when the matrix comprises an atom selected from the group of $^{13}C$, $^{15}N$, $^{29}Si$, $^{16}O$, $^{17}O$, $^{23}Na$, $^{39}K$, $^{25}Mg$, $^{40}Ca$, $^{43}Ca$ and deuterium, and the dopant is isotopically enriched.

Further described herein are methods for making and using the particles.

BRIEF DESCRIPTION OF THE DRAWINGS

The patent or application file contains at least one drawing executed in color.

Copies of this patent or patent application publication with color drawing(s) will be provided by the Office upon request and payment of the necessary fee.

DETAILED DESCRIPTION

Figure 1:
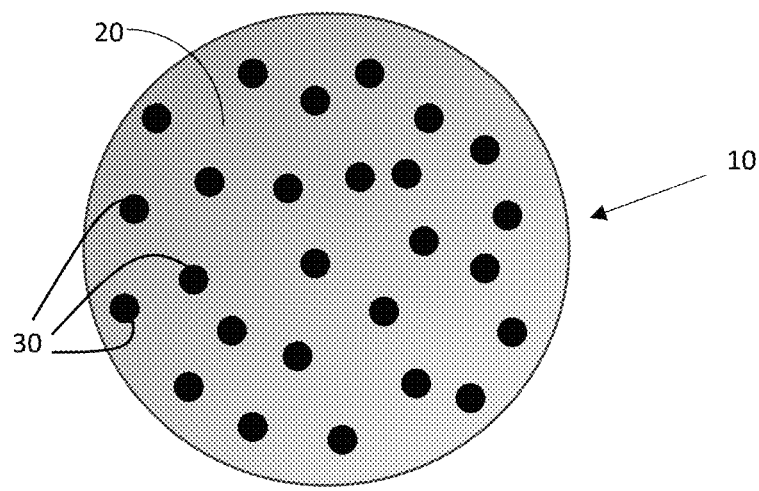
FIG. 1 depicts a particle, according to an embodiment.

Unless otherwise noted, technical terms are used according to conventional usage.

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

In case of conflict, the present specification, including explanations of terms, will control. In addition, all the materials, methods, and examples are illustrative and not intended to be limiting.

The term "subject" as used herein refers to any mammal, e.g., a human, non-human primate, horse, ferret, dog, cat, cow, rodent, swine, and goat. In a preferred embodiment, the term "subject" denotes a human, i.e., an individual.

The term "hyperpolarized" means that the nuclear magnetization of the material at hand, at ambient conditions is in exceeds $$N\tanh\left(\frac{\hbar\gamma B}{2K_B T}\right),$$

where N is the total number of spins participating in the experiment, y is the gyromagnetic ratio of the spins participating in the experiment, B is the magnetic field applied in the experiment, $K_B$ is Boltzmann's constant and T is the temperature at which the experiment is conducted and in this application refers to experiments carried out in the range of 273K to 323K.

Described herein are particles comprising a matrix and a dopant. The matrix and the dopant act together to extend the effective values of $T_1$ of probes which may be used for biological imaging. The matrix is preferably configured to have an atom having a non-zero spin nucleus, which corresponds to an atom having a non-zero spin nucleus in the dopant. For example, the matrix may comprise atoms $^{13}C$, corresponding to $^{13}C$ atoms of the dopant. The matrix may have a non-zero spin nucleus in a small percentage of the atoms of the matrix. For example, a matrix comprising calcium carbonate, which is not isotopically enriched, will still contain non-zero spin $^{13}C$ nuclei corresponding to the natural abundance of $^{13}C$. According to an embodiment, a matrix is used in which the atoms of the matrix are isotopically enriched, i.e. contain more of an isotope than the corresponding atom in its natural state, for a given non-zero spin nucleus. The matrix is preferably a crystalline substance having a longer inherent $T_1$ than the dopant, at a given temperature and magnetic field.

According to an embodiment, the matrix is a crystalline composition comprising atoms wherein one of the atoms is i. at least one of $^{19}F$ and $^{31}P$, or ii. $^{13}C$, $^{15}N$, $^{29}Si$, $^{16}$, $^{17}O$, $^{23}Na$, $^{39}K$, $^{25}Mg$, $^{40}Ca$, $^{43}Ca$, or Deuterium, optionally, isotopically enriched. Optionally, the matrix comprises a salt isotopically enriched with $^{13}C$, $^{15}N$, $^{29}Si$, $^{16}$, $^{17}O$, $^{23}Na$, $^{39}K$, $^{25}Mg$, $^{40}Ca$, $^{43}Ca$, or Deuterium. Optionally, the salt comprises one of the cations selected from the group consisting of: Na, Mg, K, Ca, and $NH_4+$, and one of the anions selected from the group consisting of: Cl, Br, $CO_3^{-2}$, $HCO_3^-$, $C_2O_4$, $PO_4$, $HPO_4$, $H_2PO_4$, $OH^-$, $NO_3$, and $NO_2$. Optionally, the anion is the carbonate ion. Optional salts may include, for example: $CaCO_3$, $Na_2CO_3$, $K_2CO_3$, $NaHCO_3$, $KHCO_3$, $LiHCO_3$, $NH_4HCO_3$, $MgCO_3$, $CaC_2O_4$, $Na_2C_2O_4$, $K_2C_2O_4$, $Li_3PO_4$, $Na_3PO_4$, $K_3PO_4$, $(NH_4)_3PO_4$, $Ca_3(PO_4)_2$, $Mg_3(PO_4)_2$, $Ca(H_2PO_4)_2$, $CaHPO_4$, $Ca_5(PO_4)_3(OH)$, $Ca_{10}(PO_4)_6(OH)_2$, $Ca_{10}(PO_4)_6F_2$, $Ca_{10}(PO_4)_6Cl_2$, and $Ca_{10}(PO_4)_6Br_2$. Most preferably, the salt is $CaCO_3$.

According to an embodiment, the matrix comprises an organic compound comprising $^{13}C$, $^{15}N$, $^{29}Si$, $^{16}O$, $^{17}O$, $^{23}Na$, $^{39}K$, $^{25}Mg$, $^{40}Ca$, $^{43}Ca$, or Deuterium. Preferably, the organic compound is an amino acid, a monosaccharide, a disaccharide, a choline, a nucleobase, a carboxylic acid, or a biological waste product.

According to an embodiment, the matrix and the dopant both comprise the atom for which the matrix is isotopically enriched. For example, if the matrix is isotopically enriched for $^{13}C$, the dopant also contains a $^{13}C$ atom, and is preferably enriched with $^{13}C$ atom.

In certain embodiments, the cations composing said salt are ions of a metal such as an alkali metal (e.g., sodium, lithium, and potassium), and alkaline earth metal (e.g., calcium and magnesium); ammonium ions ($NH_4^+$); organic cations derived from an amine of the formula $R_4N^+$, wherein each one of the Rs independently is selected from H, $C_1$-$C_{22}$, preferably $C_1$-$C_6$ alkyl, such as methyl, ethyl, propyl, isopropyl, n-butyl, sec-butyl, isobutyl, tert-butyl, n-pentyl, 2,2-dimethylpropyl, n-hexyl, and the like, phenyl, or heteroaryl such as pyridyl, imidazolyl, pyrimidinyl, and the like, or two of the Rs together with the nitrogen atom to which they are attached form a 3-7 membered ring optionally containing a further heteroatom selected from N, S and O, such as pyrrolydine, piperidine and morpholine; or a combination thereof. In certain embodiments, the anions composing said salt are organic ions such as oxalate ions and hydrogen oxalate ions; or inorganic ions such as hydroxyl ions, oxide ions, halide ions (e.g., chloride ions, bromide ions, fluoride ions, and iodide ions), dihydrogen phosphate ions, hydrogen phosphate ions, phosphate ions, polyphosphate ions such as hexametaphosphate ions and pyrophosphate ions, sulfate ions, hydrogen sulfate ions, sulfite ions, hydrogen sulfite ions (bisulfite ions), nitrate ions, carbonate ions, and bicarbonate ions; or a combination thereof. Other suitable organic anions include, without being limited to, mesylate ions, maleate ions, fumarate ions, tartrate ions, sulfonate ions (e.g., p-toluenesulfonate ions and benzenesulfonate ions), acetate ions, citrate ions, benzoate ions, and succinate ions.

Preferably, the amino acid is one of the 20 naturally occurring amino acids. Preferably, the monosaccharide is selected form the group consisting of glucose, ribose, 2-deoxyribose, arabinose, mannose, fructose, glucosamine, and xylose. Most preferably, the monosaccharide is glucose. Preferably, the carboxylic acid is formic acid, acetic acid, citric acid or pyruvic acid.

The waste product may be urea, uric acid, creatinine, or bilirubin.

According to an embodiment, the matrix is in crystalline form in the particle.

According to an embodiment the dopant is a compound involved in a biological process in a mammalian organism. The dopant is optionally selected from the group consisting of: an amino acid, a monosaccharide, a disaccharide, a choline, a nucleobase, a carboxylic acid, or a biological waste product. The dopant may be a metabolite of a biological process, such as dihyroxyacetone, choline, N-acetyl-L-aspartate, creatinine, or creatine. Optionally, the dopant is a neurotransmitter.

According to an embodiment, the neurotransmitter is selected from the group consisting of: dopamine, acetylcholine, serotonin, Gamma-aminobutyric acid, adrenaline, noradrenaline, histamine and phenethylamine.

Optionally, the dopant is a peptide, a vitamin, or a toxin. The vitamin may be selected form the group consisting of ascorbic acid, folic acid, a carotenoid, thiamine, riboflavin, niacin, pyridoxine, biotin and tocopherol.

The toxin may be nicotine, ricin, strychnine, or a mustard compound.

The dopant may be a pharmaceutical agent. Exemplary pharmaceutical agents include: S-citalopram, fluoxetine, penicillin, L-dopa, morphine, a chemotherapeutic agent, an antibiotic agent, acetylsalicylic acid, paracetamol and ibuprofen.

The dopant may be hormone. The hormone may be selected from the group consisting of melatonin, T3, T4, a steroid. The steroid may be cortisol, testosterone, estrogen or progesterone.

The dopant may be a psychoactive agent, optionally, ethanol, methanol, cannabidiol, THC, methamphetamines, cocaine, diamorphine, nicotine, or caffeine.

The dopant may be an alcohol, a glycol, glycerine, a fatty acid, a phospholipid, a lecithin, or cholesterol.

According to an embodiment, the dopant is preferably a different compound than the matrix.

According to an embodiment, a plurality of particles described above is prepared. The plurality of particles is preferably characterized by a mean particle size of between 50 and 500 nanometers. Optionally, 90% of the particles have a diameter of between 100 and 500 nm.

According to an embodiment, the amount of dopant present within the particle, in a weight/weight basis is between 0.01% to 20%, optionally from 1% to 10%.

In certain embodiments, the particle, is formulated as a suspension in an aqueous medium such as water, saline, and buffer. Optionally, a dispersant is added to the suspension.

An exemplary particle is shown in FIG. 1. FIG. 1 depicts a particle 10 having a solid, crystalline matrix 20. Within matrix 10 is dispersed dopant 30. Dispersed within the particle may be a further additive added to matrix.

According to an embodiment, the solubility in water at room temperature of a particle described herein is between: about $1\times10^{-5}$ M (mol/L) and about 6M.

Further described herein are methods for preparing particles described above. Such methods may include obtaining an isotopically enriched dopant, in an aqueous solution, combining the dopant solution with a solution comprising an ion of a matrix, for example a carbonate ion, which is optionally isotopically enriched. Then a solution comprising a counter-ion is added, to precipitate the ion of a matrix, which is optionally isotopically enriched. Upon combining and stirring, for at least a day, or at least 10 days, a precipitate is formed, comprising particles having dopant and matrix. According to an embodiment, the optionally isotopically enriched ion is a carbonate ion.

Further described herein are methods for increasing magnetic longevity in a particle, the particle comprising a matrix and a dopant, the method comprising applying homonuclear decoupling to the particle. Preferably, the homonuclear decoupling occurs after polarization of the particle, and before scanning a subject.

An advantage of compositions described herein is their ability to provide hyperpolarized probes with extended values of $T_1$. Crystalline material is often characterized by a highly ordered and rigid structure, displaying exceedingly long values of $T_1$. For example, certain samples of calcium carbonate exhibit $T_1$ values of 40 minutes. $T_1$ values of diamonds can even extend to days. Silicone crystals also exhibit very long $T_1$ values. It is suggested that the rigidity of the crystalline structure is what allows for such long T1 times. The units comprising the crystal, including the magnetic ones (such as NMR active nuclei) typically reside in very steep potential wells, meaning it requires much energy to displace them. Accordingly, the amount of thermal energy available at room temperature is only sufficient for inducing very small displacements in such ordered crystals. Conversely, in systems where the potential wells are not steep, as is sometimes the case in amorphous forms, a given amount of thermal energy at room temperature induces mechanical vibrations of relatively large amplitude. Restricting these vibrations to smaller amplitudes can significantly reduce the perturbation experienced by target nuclei, and as a result increase their $T_1$ value. Without being bound by theory, the long $T_1$ values exhibited by many crystalline solids has been demonstrated. Compositions described herein make use of that property for the sake of providing a hyperpolarized probe with sufficiently long life so as to be practical for clinical use.

According to a non-limiting embodiment, calcium carbonate nanoparticles are biocompatible, completely non-toxic at the relevant levels, and have been studied in the past as injectable vehicles for drug delivery. As will be shown in the examples, a stable suspension of enriched calcium carbonate particles has been produced and its $T_1$ value has been analyzed.

The advantage of extended $T_1$ may be applied also to include $T_1$ elongation for other organic probes, such as sugars, amino acids, vitamins, small molecule pharmaceuticals etc, which do not inherently display long $T_1$. As mentioned before, T1 processes arise from the most immediate environment of the affected nucleus and is there for highly dependent on the details of this environment. There is very little room for manipulating this environment without changing the material at hand. However, although the molecule itself cannot be manipulated, its immediate surrounding can, as demonstrated. This can be accomplished by imbedding it in a host environment that may impart on it various features that are desirable in the context of T1 elongation. For example, if a molecule of interest is hosted by an ordered and rigid crystal, its freedom to thermally vibrate may be significantly reduced. In other words, a host crystal may retain the molecule in a potential well that is steeper than the well it would reside in in its native state, and this may contribute to reduced freedom to thermally vibrate, and in turn contribute to T1 elongation.

According to another possible mechanism, Spin diffusion may be used in compositions according to embodiments of the invention to provide a long $T_1$. When spins reside close enough together, there exists a probability for them to undergo a process known as flip-flop, which essentially describes the spins exchanging their states. Accordingly, if a certain region of the sample is hyperpolarized, the spins at the borders of that region will ultimately exchange their ordered states with the spins on the other side of the border of the hyperpolarized region, effectively leaking out their magnetization, or diffusing it antiparallel to the polarization gradient—in a manner analogous to regular diffusion.

According to an embodiment, this phenomenon is present in compositions disclosed herein, in the following manner: a matrix consisting of any of the crystalline materials with long $T_1$ described above, is doped with an organic probe of interest, that displays a shorter $T_1$ value in its pure state. The process that shall occur upon release of such a doped matrix particle from the polarizer into ambient conditions is the following. The dopant organic probe with short $T_1$ will relax according to its intrinsic $T_1$ value and perhaps even faster than it would in a dissolved state (a well-known phenomenon). However, its magnetization that has been lost to relaxation shall be constantly replenished by the retained magnetization found in the matrix, by virtue of spin diffusion—from the matrix nuclei to the nuclei of the probe. Therefore, the effective time scale at which the organic probe shall remain effectively hyperpolarized is much longer than its native and unchangeable $T_1$.

It is suggested that in compositions described herein, there is leakage from the matrix polarization reservoir to the probe, which is constantly being replenished with an influx of polarization. The simulation demonstrates how a probe with a short intrinsic $T_1$ can be used as a probe for longer times, by combining with a matrix and forming particles as described herein. Further, it appears that the larger the ratio between matrix to probe, the closer the effective $T_1$ of the probe is to that of the matrix. To conclude, the compositions described herein effectively elongate $T_1$ values of organic molecular probes up to the $T_1$ value of the matrix used, as described below.

Our invention further comprises the notion of applying any of the well-known homonuclear decoupling schemes, Lee Goldberg for example, in order to suppress spin diffusion until shortly before acquisition. The rationale behind this is to prevent the leakage of matrix magnetization into the dopant probe during a time when it is not needed for acquisition and the process of magnetization diffusing from the matrix to the probe only results in its loss to the fast intrinsic relaxation of the probe molecule. If magnetization can be hindered from diffusing to the fast relaxing probe molecule it can be better preserved until shortly before the scan, at which point homo nuclear decoupling is stopped and preserved magnetization can efficiently diffuse from the matrix to the dopant molecule.

In general, the process according to an embodiment may be described as follows:
1) using particulate form of a water soluble or pH sensitive crystalline material, which contains an MR sensitive nucleus (among others) and which displays long $T_1$, as an injectable hyperpolarized probe.
2) doping the matrix comprising the particles described in 1) with an organic dopant of interest, such as a sugar, an amino acid, a vitamin, a pharmaceutical and the like, at concentrations not exceeding 20% by weight concentration. The doping is done in a manner such that the dopant molecules are dispersed in the matrix at the molecular level (as opposed to being clustered in altogether distinct domains alongside matrix domains). Doing so shall effectively elongate the $T_1$ of the organic probe, as described above.
3) using any of the well known homonuclear decoupling schemes until shortly before administering the composition to the patient being scanned, with the aim of better preserving matrix magnetization until the time when it is needed Applications In a practical aspect, embodiments described herein have the capacity to bring relief to a number of pressing clinical problems. Hyperpolarized calcium carbonate nanoparticles, being labile even to slight acidity, can be of great value in distinguishing between salvageable and irreversible ischemic injury—a pressing and unresolved problem encountered in contemporary radiology.

A further use to hyperpolarized calcium carbonate nanoparticles may be as a gadolinium contrast replacement for sensitive patients such as pregnant women, infants and neonatal infants.

Elongation of $T_1$ of organic probes embedded in crystaline matrix as dopants may provide the following capabilities, brought here just as examples from among the multitude of possible applications:
1) offer ~10 micromolar concentration sensitivity.
2) help oncology practitioners choose treatments on an informed basis.
3) monitor crucial subtleties of oncological treatment response.
4) monitor blood brain barrier permeation.

Embodiments described herein have the attribute of facilitating the survival of hyperpolarized magnetization through its journey in the circulation from injection to the site of interest, by protecting it in the safety of a crystalline micro or nano—particle.

Not only that the matrix itself can serve as a valuable hyperpolarized probe, but it can also carry organic probes and retain them in a hyperpolarized state. According to an embodiment, the particles described herein may provide a constant efflux of dissolved hyperpolarized dopant material which is by far more convenient for imaging purposes than in solid form. This is a profound advantage over previous works that focused on nano-diamonds and silicon nanocrystals as hyperpolarized long lived probes.

A function of the mineral matrix is to retain nuclear hyperpolarization during the in vivo voyage through circulation to the location of interest. It may facilitate this feat by altering the molecular environment in which the probe molecule resides in, in a manner such that the translational and rotational potential wells in which the entire probe molecule structure, including its sub constituents, reside in, is steeper that in its native state. The steepening of the potential wells translates to reduced motion for a given temperature and this in turn contributes to a decreased strength of the interaction at the spectral region that is responsible for spin lattice relaxation. The decreased interaction directly leads to decreased transition probability between Zeeman Hamiltonian eigenstates, which is synonymous with an increase in T1. In the context of spin diffusion being the mechanism responsible for T1 elongation, it is advantageous if the matrix is also be a good 'conductor' of magnetization—that is it must allow for fast spin diffusion and owing to that should contain a high concentration of the spin z nuclei of interest, albeit the concentration must not necessarily reach 100%. The crystalline matrix has a further function which is to dissolve in physiological conditions according to a desired profile and release the hyperpolarized nuclei that reside within it into the surrounding in dissolved form, which is suitable for detection in an imaging scheme, as opposed the hyperpolarized solid phase which is unsuitable for imaging.

A function of the dopant is to serve as a hyperpolarized probe for some biochemical process in the body which is of clinical interest. As such, the dopant should be a substrate participating in such a biochemical process and the native atoms consisting it must be isotopically enriched with an adequate corresponding spin ½ isotope, to the extent that such enrichment is necessary (for example for P, 100% of naturally occurring nuclei have the atomic number of 31 and possess spin ½, hence no enrichment is needed in this case. However, for carbon, only ~1% of naturally occurring nuclei have the atomic number of 13 and a spin of ½, so in this case enrichment is preferred).

A function of the additive is to impart the desirable dissolution profile to the mineral matrix so as to assist its dissolution in the time window relevant for conducting hyperpolarization assisted MRI scan. The additive may be used to impart other desirable traits to the particle, such as stability. For example, the stable form of calcium carbonate is the mineral calcite. This mineral has very poor water solubility. The polymorph vaterite on the other hand, has better solubility, but is unstable and a batch of vaterite powder may transform spontaneously to calcite if left for several days, even at ambient conditions. However, incorporating aspartic acid in vaterite stabilizes it and is known to prevent the transformation to calcite. Since the additive is generally not intended for MRI observation, its isotopic composition is of lesser importance, and it does not require enrichment with spin ½ possessing nuclei. For the sake of retaining long $T_1$ for the entire composite particle, one may even want to eliminate such nuclei from the additive (for example have it deuterated).

Another example for an additive is water in glucose matrix. As demonstrate in example 1B, the hydrate form of glucose displays longer $T_1$ than the anhydrous form. In this context, water, or preferably heavy water, may be an additive that improves the relaxation properties of the matrix.

Considering such particles, the process of clinical utilization of them can be done as follows:

Polarizable formulation. A polarizable formulation should consist of the particles of interest mixed with polarizing agents which are basically unpaired electrons, also known as free radicals, or paramagnetic centers. During the process of hyperpolarization, magnetization is transferred from the polarizing agents to their immediate surrounding. Polarization then diffuses throughout the particles sample via spin diffusion. Consequently, it is preferable that the distance polarization must diffuse be as short as possible, for this process is known to be slow.

To realize this, several examples of formulations can be given:

Polarizable formulation 1: particles are suspended in a glassing solution with traditional polarizing agents. One way to prepare this formulation is to prepare 50/50 w/w solution of glucose, either $^{13}C$ labeled, at any position and to any percentage or not, in water, $D_2O$ or a mixture thereof—this constitutes a glassing solution. To this solution, OX063 is added to a final concentration of 15 mM. optionally, paramagnetic gadolinium (Gd-DOTA) can be added to a final concentration of 0.3 mM. In this formulation, the particles are suspended in the hyperpolarizing matrix. Polarization diffuses across the solution/particle interface into the particle and eventually polarizes the particle's bulk substantially.

Polarizable formulation 2: particles are suspended in are suspended in a glassing solution with traditional polarizing agents. The glassing solution is composed of toluene/THF at a ratio of 8:2 by volume. Solvents may be enriched, uniformly, sparsely, with $C^{13}$, with Deuterium, to 100% or to a lesser extent and with any combination of the above. Solvents are supplemented with TEMPO radical to a concentration of between 10 and 80 mM.

Gamma irradiated particles: the particles can be imparted with polarizing agents by means of gamma irradiation. Particles can be prepared in their final form and subjected to gamma irradiation from any conventional source, such as $^{60}Co$ rods. The preferred dose should be between 1 KGy and 400 KGy. The particles thus irradiated can be hyperpolarized using the radiation induced paramagnetic centers formed in them as polarizing agents. The particles may be heled in isolated conditions in the period between irradiation and hyperpolarization, to help preservation of the formed polarizing agents. Such conditions may include keeping them in a sealed vessel with a controlled atmosphere that can be either an inert gas or even a moderate vacuum. Another option is to keep the particles under low temperature (anywhere between room temperature and 76 K). this particular method has the advantage that particles can be used in their final formulation without any further processing. It has the disadvantage of implanting paramagnetic centers within the matrix of the particles that may significantly shorten $T_1$, and cannot be rid of until particle dissolution.

Plasma activation: particles are exposed to ionized gas (see U.S. Pat. No. 10,718,840). Paramagnetic centers are formed by virtue of energetic particles from the plasma impinging on the particles. Particles can then be hyperpolarized as needed and are subsequently ready for use.

Blending of particles into solid matrix. Particles can be blended into a matrix that consists of a solid material that has been imparted with polarizing agents by means of plasma exposure, ionizing radiation or by any other means. The matrix thus formed is roughly mixed with the particles and the heterogeneous mass is extruded through a press roller. The resultant 'filament' mass is folded and passed again through the roller. By repeating this process for a number of times, extremely close molecular level contact can be achieved, without resorting to drastic phase changes such as melting or dissolution, which are bound to be detrimental for gamma and plasma induced radicals or for any other type of labile radicals.

Hyperpolarization. The step of DNP hyperpolarization can be performed by any of the established techniques known in the field. The basic scheme is simply placing the polarizable sample in a magnetic field at a temperature of a few kelvins or less, and irradiating it at a frequency roughly equal to the sum or difference of the electron and nuclear Larmor frequencies. Various slightly more advanced variants can also be employed such as off resonance CP like polarization transfer (Sheetal et al., *The Journal of Chemical Physics*, 2017, 147, 164201), MW frequency modulation (Y. Hovav, A. Feintuch, S. Vega, D. Goldfarb, 2014, *Journal of Magnetic Resonance*, 2014, 238, 94-105), proton DNP with CP assisted polarization transfer (Transportable hyperpolarized metabolites, *Nature Communications*, 2017, 8, 13975) etc.

Dissolution. The step of dissolution is to be performed by standard techniques available in the field.

Further processing. This step is meant to condition the hyperpolarized nanoparticles to administration. As such, it must be fast and not take more than a few seconds to tens of seconds at the maximum. This step is required to carry out the elimination persistent polarizing agents (such as OX063), replacing the solvent with aqueous medium, eliminating particles that exceed the maximal size that is safe for injection, or any combination of the aforementioned actions. The means by which these actions are carried out are in some cases already formulated (OX063 elimination, size cutoff).

Injection. This step is to be performed in an automated manner and according to well-known and established techniques. The only feature that may be unique to our case is, and it too is well recognized in the hyperpolarization field, is the need to maintain the sample in a magnetic field for as much of the path from dissolution apparatus to needle. The reason is that without the presence of an external magnetic field rapid loss of magnetization occurs and this phenomenon is exacerbated in solids.

Distribution in the body. In this stage, the injected particles travel with circulation to the site of interest and permeate through blood vessel walls. However, a number of steps may be taken to protect the magnetization from fading during the voyage stage. In the context of spin diffusion $T_1$ elongation mechanism, although the intrinsic relaxation of the crystalline matrix cannot be extended, fast relaxation may occur at the metabolic probes embedded in the matrix, and during the particles' transition from outside of the body to the site within the body that is to be imaged, it may constantly consume magnetization flowing to it through spin diffusion from the matrix. Halting spin diffusion for the period of the voyage may protect magnetization stored matrix. Shortly before the scan after most of the particles' transition has ended, spin diffusion may be allowed to proceed again. Spin diffusion may be halted or inhibited by virtue of decoupling the spins from one another. This can be done using the Lee-Goldberg technique for example. Alternatively, actual rotation of the particles about the magic angle may be externally induced using dielectrophoretic fields. For this option to be effective, suitable modifications to the particles may be required, such as non-isotropic modifications of the dielectric constant. A further option may be to design the particles to display a large zeta potential for a duration typical of the voyage, this shall allow the particle to remain freely suspended and tumble about itself in a manner than may possibly decouple the spins from one another. At the end of the time window designated for the transition, the isolating properties of the high zeta potential can be designed to abruptly deteriorate, causing it to adhere to its surrounding and lose its mobility, thereby restoring the coupling between the spins, and alleviating the hindrance to spin diffusion.

Scan. The scan is to be performed using techniques well known in the field of MRI and MRI of hyperpolarized agents.

The particles. Particles should ideally posses a number of features. They should comprise from a matrix characterized by long $T_1$ times. Particles should, under ambient conditions and a magnetic field in the range of from about 0.5 tesla (0.5 T) to about 20 T, a substantially long spin-lattice relaxation time ($T_1$), i.e., in the range of from about 30 seconds to about 1 hour, e.g., from about 1 minute to about 45 minutes, from about 2 minutes to about 40 minutes, from about 4 minutes to about 30 minutes, or from about 8 minutes to about 20 minutes.

They should dissolve in physiological conditions over several minutes. They should, in some embodiment, include a biochemical substrate that is an organic molecule at an amount of about 0.01 to about 20% by weight of the matrix, homogeneously dispersed through it. The mineral matrix forming the particles should optionally be enriched up to 100% with the spin ½ isotope of the corresponding element comprising it to facilitate efficient spin diffusion. The mineral matrix should have at least a small amount of water solubility so as to facilitate dissolution in vivo. The particles should not exceed a gross size of ~10 um—above that capillary obstruction may result. Preferably, particles should be much smaller, in the range of 100-200 nm or so. In physiological conditions particles should have a zeta potential exceeding −10 mV, preferably exceeding −30 mV, to preclude any chance of aggregation. We note that the zeta potential of the particles in conditions other than physiological is not subject to such a constraint. The preferable spin ½ nuclei for our application are $^{13}C$, $^{31}P$, $^{19}F$, $^{15}N$ and perhaps $Na^{23}$. consequently, our matrix should comprise of any or the following ions: $CO_3$, $HCO_3$, $DCO_3$, $C_2O_4$, $PO_4$, $HPO_4$, $H_2PO_4$, $DPO_4$, $D_2PO_4$, $HDPO_4$, $F^-$, $Na^+$, $H4N^+$ (and deuterated forms), $NO_3^-$. The partner ions may be any ion that is physiologically tolerable in significant amounts such as: Na, K, Ca, Mg, Cl, $SO_4$ and to a lesser extent Br and I.

As dopants (traceable substrates) one may consider compounds that participate in important biochemical processes in the body such as pyruvate, glucose, mannose, fructose and various other simple sugars, all the amino acids, cytosine, guanine, adenine, uracil thymine, urea, cholesterol, choline, dopamine, serotonin, acetyl choline, various pharmaceuticals such as aspirin, paracetamol, penicillin (of various kinds), nitrogen mustards, alkaloids, antimetabolites, antineoplastic agents and the like.

Nanoparticles can be produced by multiple methods, as described below: Grinding: $^{13}C$ enriched $CaCO_3$ is prepared. Dissolve 3.4 g of 99.9% $^{13}C$ enriched $NaHCO_3$ in a 1M solution of NaOH to a final volume of 25 ml to form a carbonate solution. Dissolve 5 g of anhydrous $CaCl_2$) in DD water to a final volume of 115 ml to form a calcium solution. Place the calcium solution on a magnetic stirrer in a 250 ml beaker under constant stirring at 600 RPM. Add the carbonate solution to the calcium solution within less than 5 seconds. Leave the reaction beaker on the stirrer for one hour. Centrifuge the precipitate and proceed to rinse and centrifuge for an additional two times. Place the precipitate in an oven set to 90° C. for about 5 hours. Proceed to grind the dried $CaCO_3$ in a planetary mill. Place the $CaCO_3$ in a 80 ml zirconia vessel and add 25 zirconia balls, 10 mm in diameter. Add 8 g of DD water. Add 3 drops of dispersant Dolapix-pcn. Set the mill to 16 cycles of 22 minutes of milling at 400 RPM followed by 30 minutes of rest. A thick past consisting of pure, 99.9% $C^{13}$ enriched $CaCO_3$ nanoparticles results.

Flash precipitation 1: to a 50 ml falcon add 4 ml of $CaCl_2$) 1M solution (Ca wise). To a second falcon add 40 ml of 99.9% $^{13}C$ enriched $Na_2CO_3$ at a concentration of 100 mM (carbonate wise). Pour the 40 ml of solution into the falcon containing the 4 ml of solution. Cap the falcon and shake vigorously. Centrifuge for 3 minutes. Decant the supernatant and introduce ethanol instead. Mix well to extract the water from all parts of the sample. Centrifuge and decant again. Repeat thus described ethanol rinse once again. Place the precipitate on oven set to 70° C. for 10 hours. Sample is ready. Sifting is required to separate the tens of nm's amorphous/vaterite particles from large particles of calcite typically measuring 1-2 microns. Flash precipitation 2: place a glass tube on a clamp with an ultrasound finger inside it. Add 5 ml of $CaCl_2$) 200 mM solution (Ca wise). Activate sonication and using a syringe, while sonication is on, abruptly add 1 ml of 99.9 $^{13}C$ enriched $NaCO_3$ 1M solution. Pour the content of the glass tube into a Dewar with liquid nitrogen. Collect the formed beads and lyophilize them to rid of the water. Nanoparticles are ready. Particles appear to be in the size range of 0.5-2 μm. Although this is quite large, they are believed to be $NaCl/CaCO_3$ composites and as such upon contact with an aqueous medium they are expected to lose ~60% of their volume on account of NaCl dissolution, and more importantly, disintegrate.

Slow precipitation: to a 250 ml beaker, placed on a magnetic stirrer, add 100 ml solution of 99.9% $^{13}C$ enriched $NaHCO_3$ at a concentration of 50 mM and uniformly $^{13}C$ enriched L-aspartic acid at a concentration of 25 mM. in a separate vessel, prepare 100 ml solution of $CaCl_2$) at a concentration of 50 mM and uniformly $^{13}C$ enriched L-aspartic acid at a concentration of 25 mM. titrate both solutions with HCl and NaOH to neutral pH. Using a syringe pump, add the former solution to the previous at a rate of ~1 ml/min while stirring. Filter the precipitate and place in oven set to 70 C for 10 hours. A powder of vaterite doped with aspartic acid (~1.6% w/w) is formed. The size of the crystals is many microns and must be reduced by any of the common techniques used to reduce particle sizes such as milling, sonication or homogenization.

The following examples are provided to illustrate certain particular features and/or embodiments. These examples should not be construed to limit the disclosure to the particular features or embodiments described.

Example 1A: Production of Calcium Carbonate Particles

The following materials were added to a zirconia vessel of a planetary ball mill: 1.221 g of $Ca^{13}CO_3$, 4 g of $CaCO3$, 25 zirconia balls 10 mm in diameter, 8 g of double distilled (DD) water, 3 drops (approximately 150 mg) of dispersant 'Dolapix PCN' by Zschimmer-Schwarz. The mixture was milled for 16 rounds each consisting of 22 minutes of work at 400 RPM followed by 30 minutes rest. Milling was conducted in a Fritsch planetary ball mill in a 89 ml zirconia vessel with 25 zirconia balls, 10 mm in diameter. The resultant slurry proved to form a stable aqueous suspension upon addition of water, as shown below. The T1 properties of the slurry were analyzed using a Bruker 200 MHZ NMR spectrometer, using a variable recycle delay (and using dummy scans when needed) to probe the T1 of the resultant material. In addition to the slurry, three other forms were tested: A dried form of calcium carbonated was prepared by placing 410 mg of the paste (slurry) on a glass plate and drying overnight in a stabilized oven at 65 C. 182 mg remained, which was then crushed manually and measured. To form an annealed sample, the dried calcium carbonate was annealed in an oven for 9 hours at 400° C. To form a rewetted sample, a bit of tap water was added to wet completely all the powder with some excess.

The slurry had a $T_1$ value of 284 seconds. The dried composition had a $T_1$ value of 349 seconds. The annealed composition had a $T_1$ value of 432 seconds. The rewetted composition had a $T_1$ value of 367 seconds. As can be seen, the batches prepared by these processes yielded $T_1$ values between almost 5 and 7 minutes. The return of $T_1$ to around 6 minutes upon rewetting of the slurry indicates that water proton mediated relaxation is at play here and is at fault for reducing $T_1$ from over 7 minutes to around 6. This problem may be resolved by using $D_2O$ instead of regular water as a solvent for suspension.

Figure 2A:
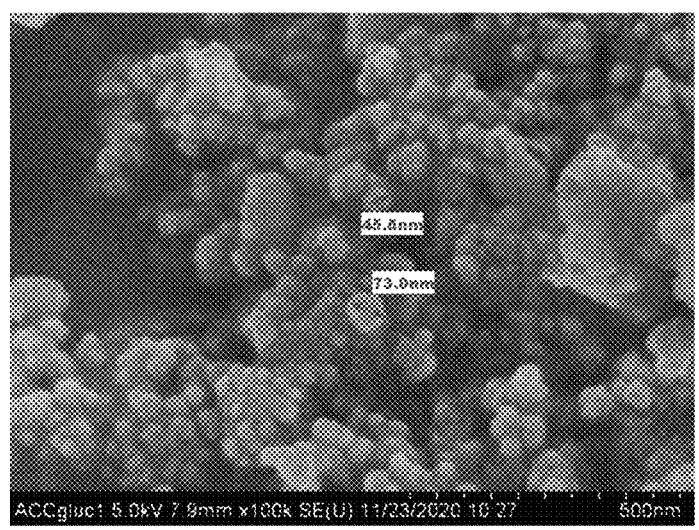
FIGS. 2A-C depict scanning electron micrographs of calcium carbonate particles.
Figure 2B:
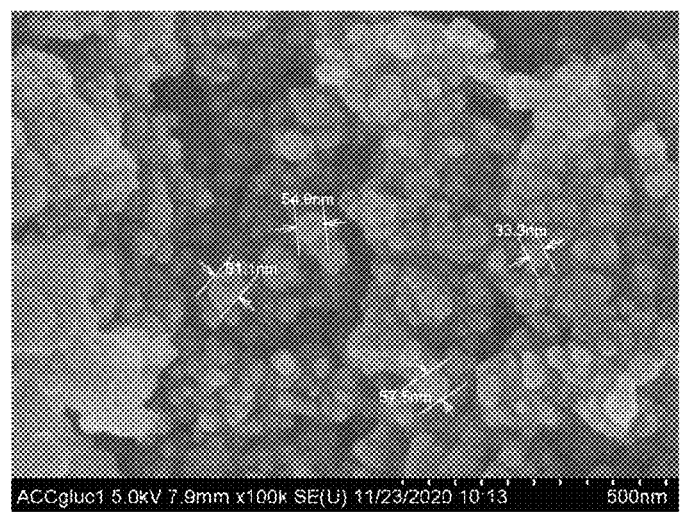
Figure 2C:
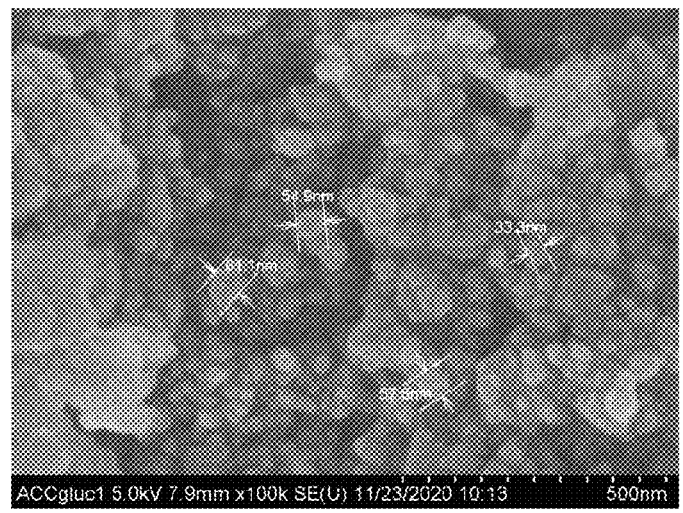

Reference is made to FIGS. 2A-C showing scanning electron microscope images of calcium carbonate particles prepared as described above. As can be seen, particles are in the range of size between 30 and 70 nm.

Four suspensions of calcium carbonate particles described above were prepared using the slurry, diluted by a factor of 8 with water, using ultrasound for suspension homogenization. The suspensions differed in the dispersant used: no dispersant, Dolapix ET85, Dolapix CE64, Dolapix PCN. The dispersants are each commercially available dispersants comprising carbonic acid esters. To inspect suspension stability, suspensions were added to transparent straws and were left to stand veritcally for 37.5 hours, after which the state of the suspension could be visually inspected. All of the samples prepared using dispersant were stable. The suspension made using Dolapix PCN was the most stable, as most of the particles remained in suspension.

Figure 3:
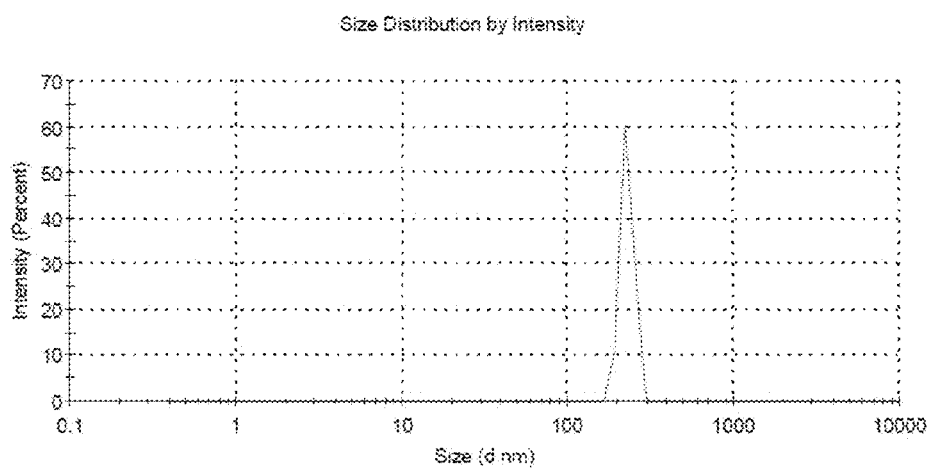
FIG. 3 depicts a graph showing particle size of calcium carbonate particles in suspension as shown by light scattering methods.

The suspension prepared using Dolapix ET85 was measured using a Malvern Zetasizer dynamic light scattering apparatus, and the results of the particle size are shown in FIG. 3, showing a narrow size distribution at about 230 nm.

This example shows that calcium carbonate particles in nanometer (10-500 nm) range retain a long T1, even while in form of a slurry.

It is expected that various water soluble, sparsely soluble or pH sensitive minerals would also display long $T_1$ values, and shows that it is not physically impossible for nanoparticles in suspension to exhibit long T1 values. Such minerals include, but are not limited to, sodium carbonate, potassium carbonate, magnesium carbonate, sodium phosphate, and calcium phosphate. It is preferred that matrix is preferably at least somewhat soluble in order to release dopant molecules after administration to a human body, having a solubility of at least $1 \times 10^{-5}$ M. Some minerals which are completely insoluble, would be ineffective as matrix molecules, for example, quartz and diamond, as they would not release dopant upon administration in a human body and therefore could not be considered to be used for the uses described herein.

Example 1B—Crystalline Glucose Nanoparticles

As shown below, glucose in its crystalline form can also display exceptionally long T1 values. For this demonstration data from three samples of glucose were used: samples A, B and C. Sample A is glucose which is isotopically enriched to 100% with $^{13}C$ in all 6 positions, and with $^2H$ in all 7 nonexchangeable positions, as received from the vendor without any further treatment. Sample B used the same starting material as sample A but was subjected to the treatment as follows: a portion of isotopically enriched glucose together with two portions of regular glucose were dissolved in 30 portions of heavy water. The solution was heated so as to evaporate most of the heavy water, leaving a homogeneous mixture of enriched and non-enriched glucose, with the relative ratio of 1 to 2, respectively, and with deuterium nuclei occupying the vast majority of exchangeable proton sites. The material was left to crystalize, and the resultant crystalline mass was further dried overnight in an oven set to a moderate temperature.

Figure 4:
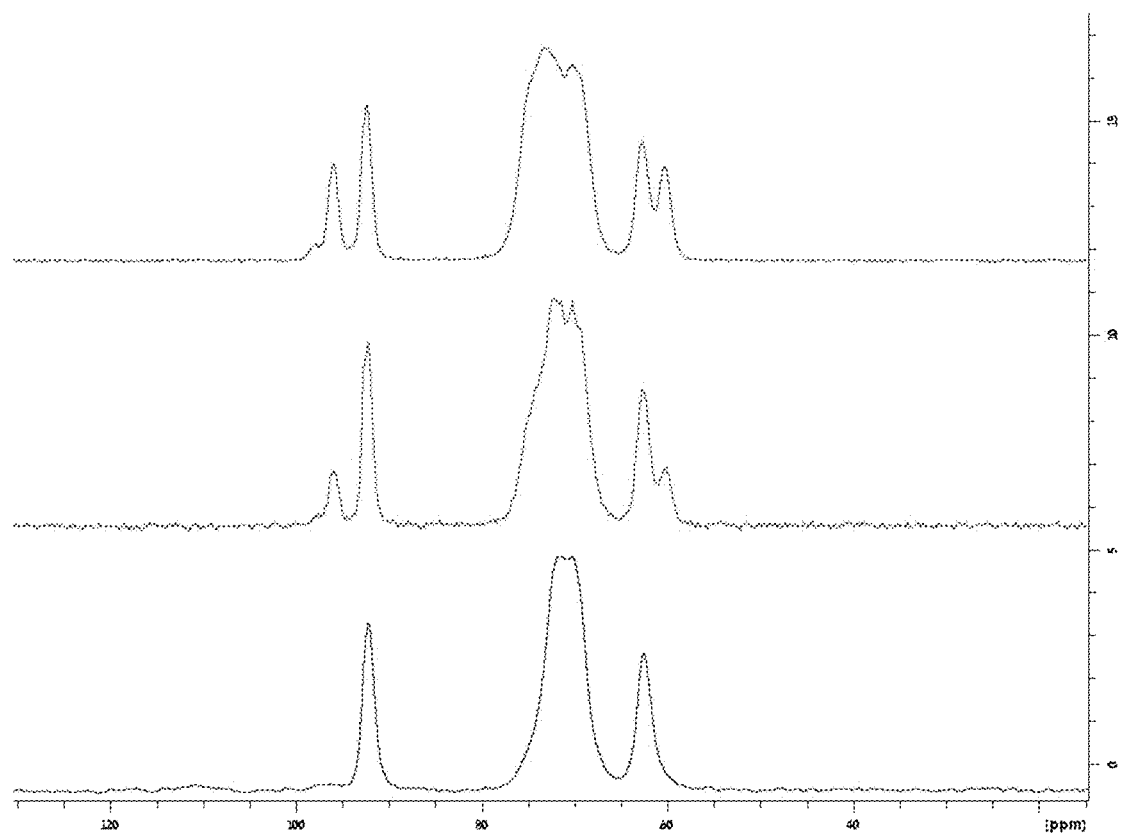
FIG. 4 depicts X-ray diffraction spectra of three types of glucose particles.

Sample C was of nano sized glucose consisting of particles in the size range of 50-150 nm and was prepared according to the following protocol: glucose was ground twice by mortar and pestle. The ground powder was added to isopropyl alcohol at great excess and sonicated for about 10-20 minutes. the suspension was then left to stand in a narrow vessel for about 20 minutes. This duration allowed for all large particles to sink with only the finest particles remaining suspended. The suspension was then decanted, leaving behind the fraction of coarse particles. It was then centrifuged, and the medium was replaced from IPA to acetonitrile. The suspension of fine glucose NPs in acetonitrile was frozen in liquid nitrogen and lyophilized. FIG. 4 presents the spectra obtained for these three samples. The upper XRD spectrum is of sample A. The middle XRD spectrum is of sample B and the lower XRD spectrum is of sample C. A detailed examination of the spectra reveals that 4 types of glucose are present. A hydrate and an anhydrous form are evident by the peaks at 95.9 ppm and 92.5 ppm respectively. One can also observe such behavior for the peaks residing at 62.8 ppm and 60.3 ppm, which anhydrous alfa form for the higher shift peak, and to either a beta form or a hydrated alfa from for the lower shift peak.

The inventors observed that the $T_1$ for the anhydrous form of the glucose, found exclusively in the nano-sized sample is about 350 sec, while the $T_1$ found for the hydrate alfa or the beta form, found in various portions in samples A and sample B displays values of 500 and even 570 seconds. The conclusion to be made from this is that there are many crystalline solids that are organic molecules, which display exceedingly long $T_1$ values and many of which are completely benign, non toxic and safe for injection. Further, many of them participate in important metabolic processes in the body and are thus promising candidates as hyperpolarized metabolic probes in their own right. Other potential biologically active molecules which can be used include solids such as sodium bicarbonate, potassium bicarbonate, fructose, mannose, xylose, sucrose, sodium pyruvate, sodium fumarate, acetate salts, other carboxylic acids salts, other simple sugars, amino acids, nucleic acids, vitamins, neurotransmitters, pro-neurotransmitters, drugs and pro-drugs.

Example 2: Matrix-Dopant Particles Displaying Spin Diffusion

Particles of sodium carbonate matrix with aspartic acid as a dopant were prepared to demonstrate spin diffusion. An aqueous solution of 0.35 mg/ml of uniformly labeled 100% $^{13}C$ enriched L aspartic acid and 50 mM sodium carbonate, with the carbonate also enriched with $C^{13}$ to 100% was prepared. An additional solution with the same concentration of enriched aspartic acid and 50 mM $CaCl_2$) was prepared The two solutions were mixed at a rate of 1.5 ml/min under stirring and slightly elevated temperature (plate set to 60° C.). After mixing, the precipitant was let to mature in the reaction vessel under stirring and elevated temperature for 11 days. The precipitant was separated from the solution and rinsed to remove any aspartic acid that is not internally incorporated in the $CaCO_3$ matrix. The formed material was dried.

Figure 5:
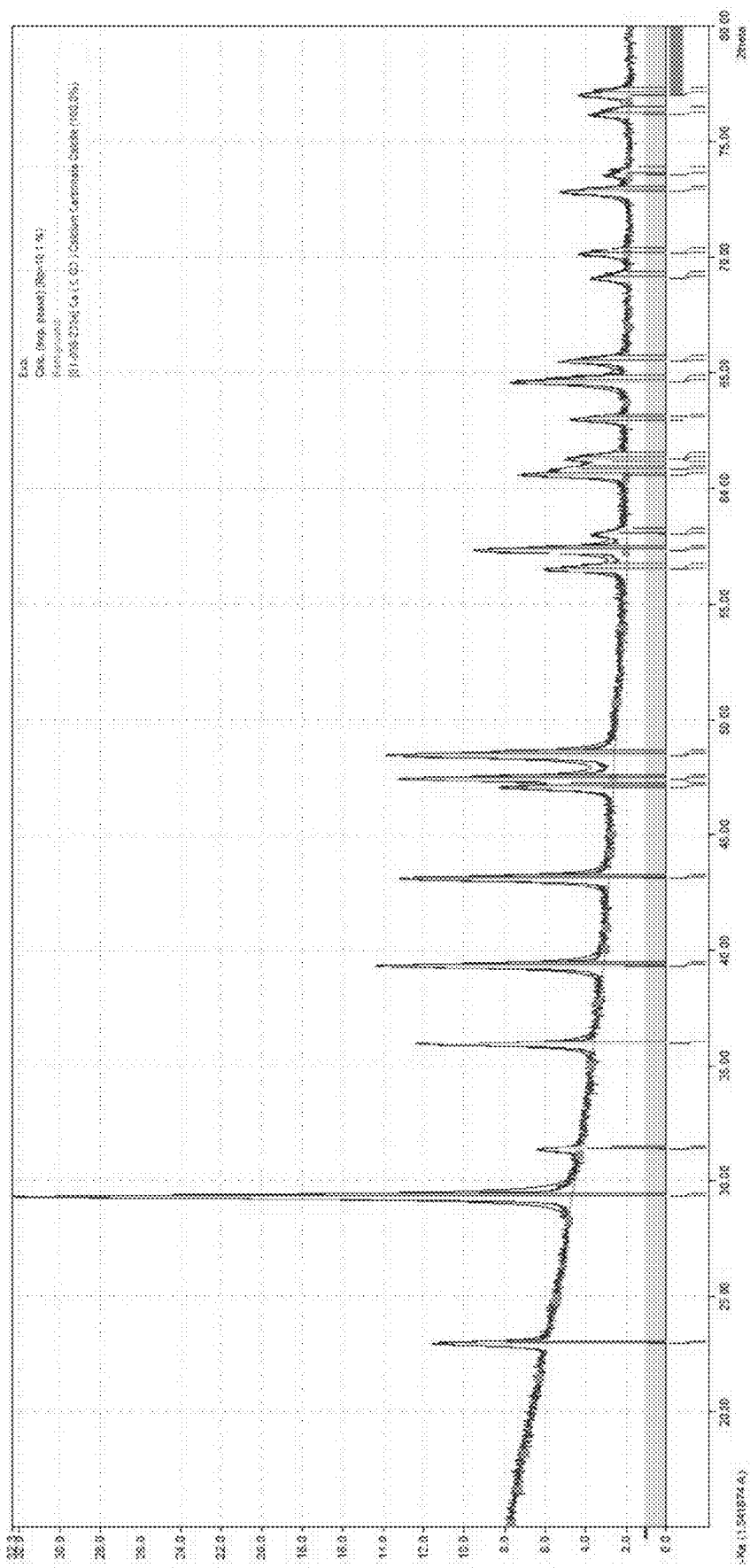
FIG. 5 depicts an X-ray diffraction spectra of calcium carbonate particles according to an embodiment.

An XRD spectrum of the material thus produced is presented in FIG. 5, showing that calcite was formed.

The material was subject to elemental analysis which showed that aspartic acid is incorporated at a molar concentration of ~0.44%.

Figure 6:
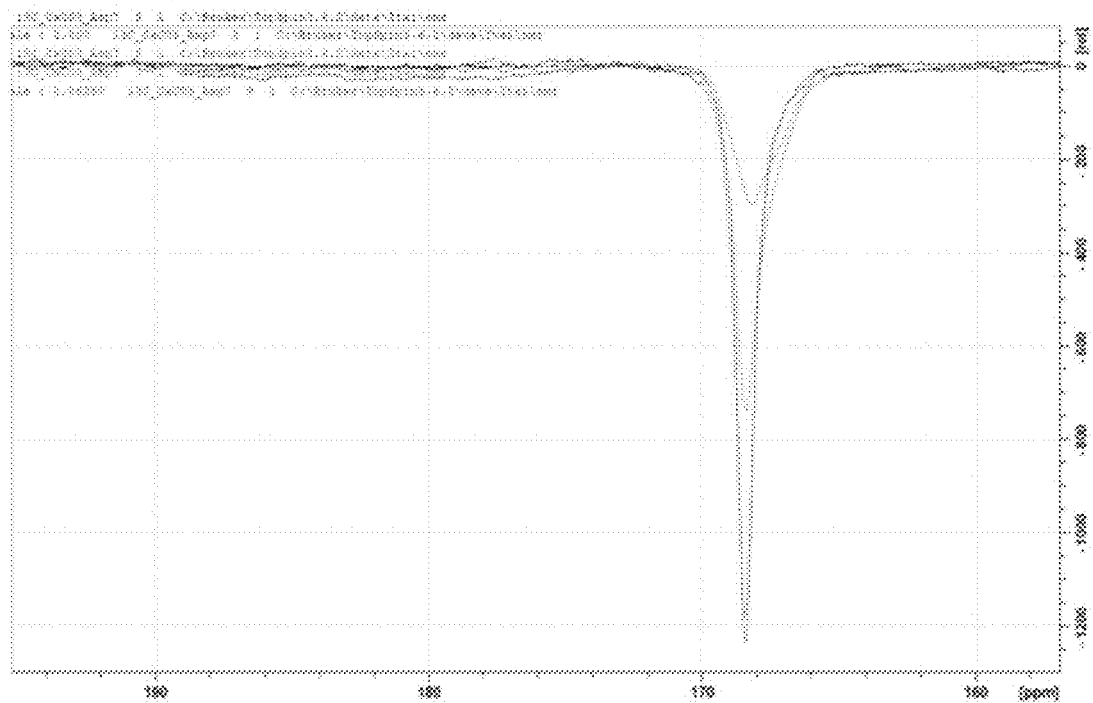
FIGS. 6 and 7 depict $^{13}C$ NMR spectra showing carbonate peak of particles having calcium carbonate as a matrix, and L-aspartic acid as a dopant, at various time points as a result of cross polarization.

Measurements of spin diffusion were carried out by virtue of selectively polarizing the carbons of the aspartic acid using cross polarization and the carbonate carbons in the immediate vicinity of the aspartic acid molecules and observing the system after spin diffusion was left to proceed for various durations. This example was performed by polarizing the carbons bound to hydrogen atoms selectively (in the aspartic acid molecules) while not directly polarizing the carbonate carbon atoms. The results of this experiment appear in FIG. 6 which show a $^{13}C$ NMR spectra after various time points, of a carbonate-carbon peak, and demonstrate strong contact between the organic and inorganic $^{13}C$ nuclei, and spin diffusion between them. The spectra are shown after spin diffusion was left to proceed for 10 milliseconds (ms) (green), 1 sec (red), 5 sec (purple) and 10 sec (blue). As can be seen, the green peak is shallowest, followed by red, purple, and blue, which is the deepest. In this example, carbons of the dopant were selectively magnetized, and the magnetization of carbons of the matrix, which were not directly magnetized, but were indirectly magnetized through spin diffusion, are shown to depend on length of contact with the dopant molecules. The matrix carbonate peak grows as a result of the increased magnetization from the selectively polarized carbons of the aspartic acid dopant diffusing to the matrix. This demonstrates that efficient magnetization 'conductivity' exists between the organic carbons in the dopant and the carbons in the mineral crystalline matrix. It is suggested that conversely, magnetization conductivity may also conduct magnetization from the matrix, having a longer $T_1$ time, to dopant, having a shorter inherent $T_1$, thereby allowing extended use of dopants by preparing them within particles with matrix as described herein.

Figure 7:
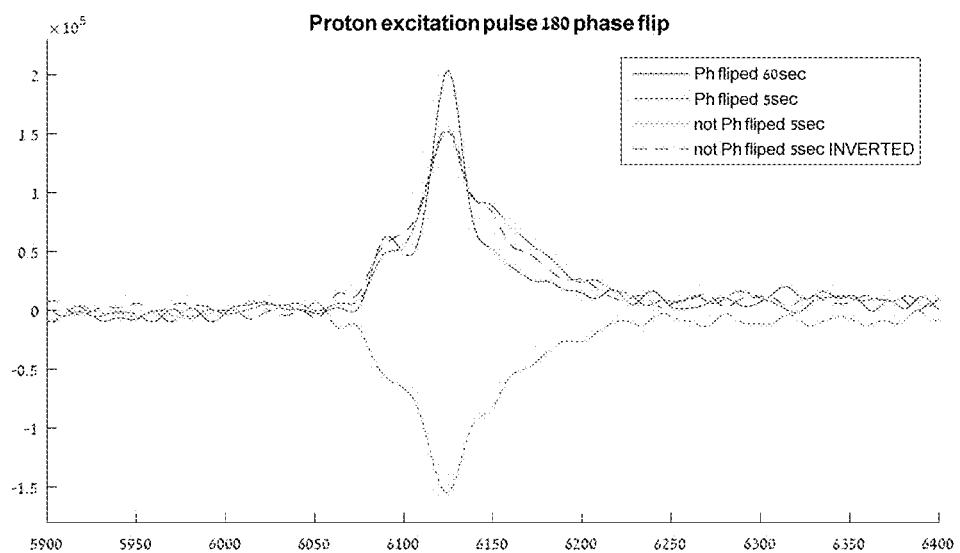

A further support to these results can be found in results obtained with similar spin diffusion experiment conducted with a similar sample but with a matrix enrichment of 10% instead of 100% and without $^{13}C$ enrichment of the aspartic acid. The results of this experiment are presented in FIG. 7. FIG. 7 shows a broad, lower peak (in red) of a phase-flipped measurement after 5 seconds, and narrower, higher peak, in blue of a phase-flipped measurement after 60 seconds. The "not phase flipped peak" was after 5 seconds and is shown in yellow, and its corresponding inverted peak is shown in dotted line, indicating that the phase flipped peaks are accurate and are not an artifact. Here too, polarization was imparted selectively to protons, thereby exciting the aspartic acid $^{13}C$ atoms, which although the sample was not isotopically enriched, were present in naturally occurring concentrations. The magnetization of the immediate vicinity of the aspartic acid molecules, which were not in crystalline form, as suggested by the broad peak, diffused from nearby carbonates (broad peak) over time between the 5 second and 60 second measurements, to more distant ones in the crystalline regions of the matrix, to form a narrower peak. It is evident that the carbonate peak does not gain much intensity on account of the fact that there is hardly any polarization stored in the organic phase, which has only naturally occurring $^{13}C$ nuclei and these are found at a very small concentration.

Example 3—Reverse Spin Diffusion

An experiment that demonstrates the diffusion of magnetization from the matrix to the organic probe was performed.

Figure 8:
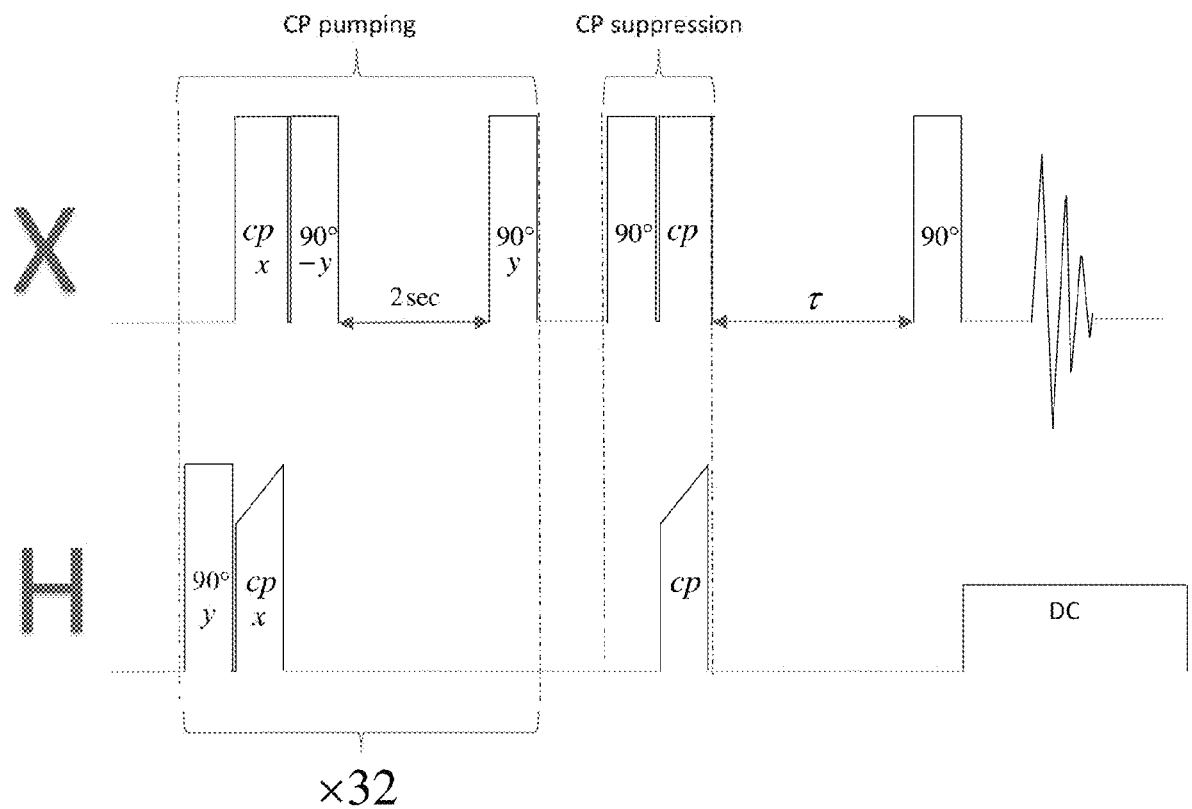
FIG. 8 depicts a diagram showing polarization procedures performed to selectively polarize a matrix according to an embodiment.

Owing to the small concentration of dopant in the sample and the long relaxation times, it is impractical to gather data based on direct excitation and one must rely on cross polarization from protons. However, since protons are found predominantly on the aspartic acid molecule, and since spin diffusion progresses so efficiently in the sample, any polarization attained on or near the aspartic acid rapidly diffuses away to the rest of the calcite matrix. This results in a significant matrix signal and in an aspartic acid signal depressed to a point where it cannot be observed. To overcome this, a pulse sequence was designed which repeats the process of cross polarization-spin diffusion multiple times. This results in the matrix being saturated with magnetization, to the point that diffusion from the cross polarized aspartic acid all but stops. In order to highlight the diffusion from the matrix back to the aspartic acid, consecutive to this polarization pumping to the matrix is a block that suppresses the polarization of the aspartic acid by way of reverse cross polarization (from carbons to protons rather than from protons to carbons). Following that, spin diffusion in the sample is allowed to proceed for a variable duration of $\tau$, at the end of which the signal is acquired. This pulse sequence, which has been called 'CP pump reverse spin diffusion' is depicted in FIG. 8. The X row in FIG. 8 depicts pulses applied to Carbon and row depicts pulses applied to protons.

This pulse sequence was applied to two samples discussed in Example 2, one sample (sample D) in which the carbon atoms of the carbonate ion in the matrix were isotopically enriched, and one sample (sample E) in which the carbon atoms of the matrix were not isotopically enriched. This was performed to show the mechanism by which T1 is effectively elongated and determine whether it is a result of spin diffusion or of the altered molecular environment of the entrapped aspartic acid.

Figure 9A:
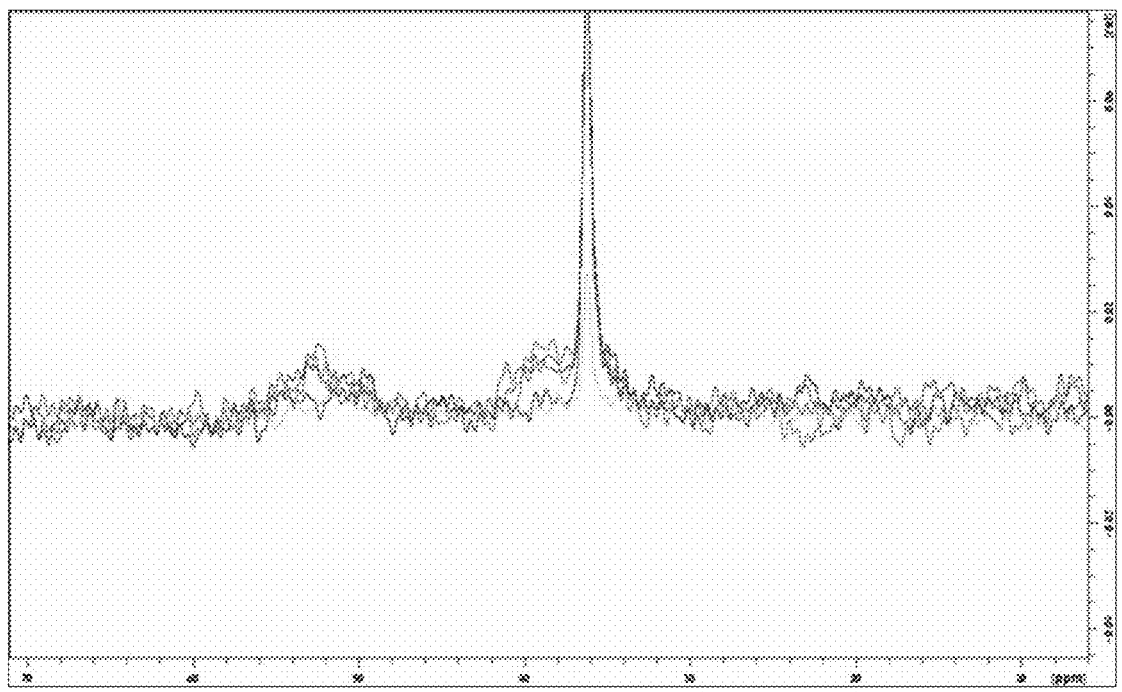
FIGS. 9A, 9B, 10A and 10B depict $^{13}C$ NMR spectra showing carbonate peak of particles having calcium carbonate as a matrix, and L-aspartic acid as a dopant.
Figure 9B:
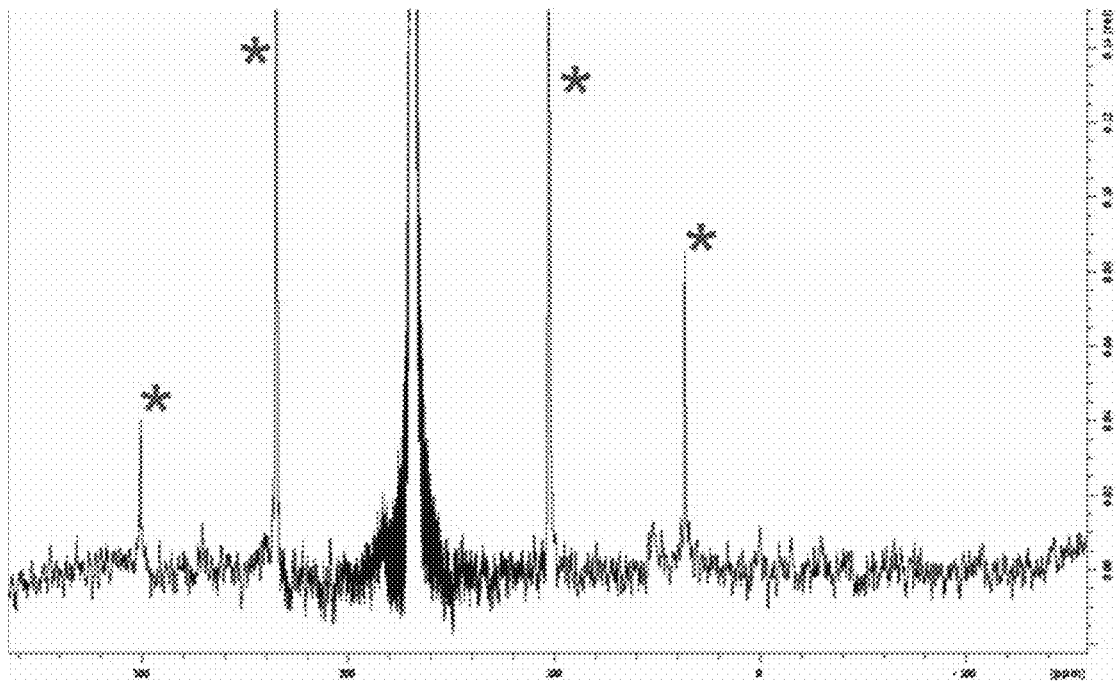
Figure 10A:
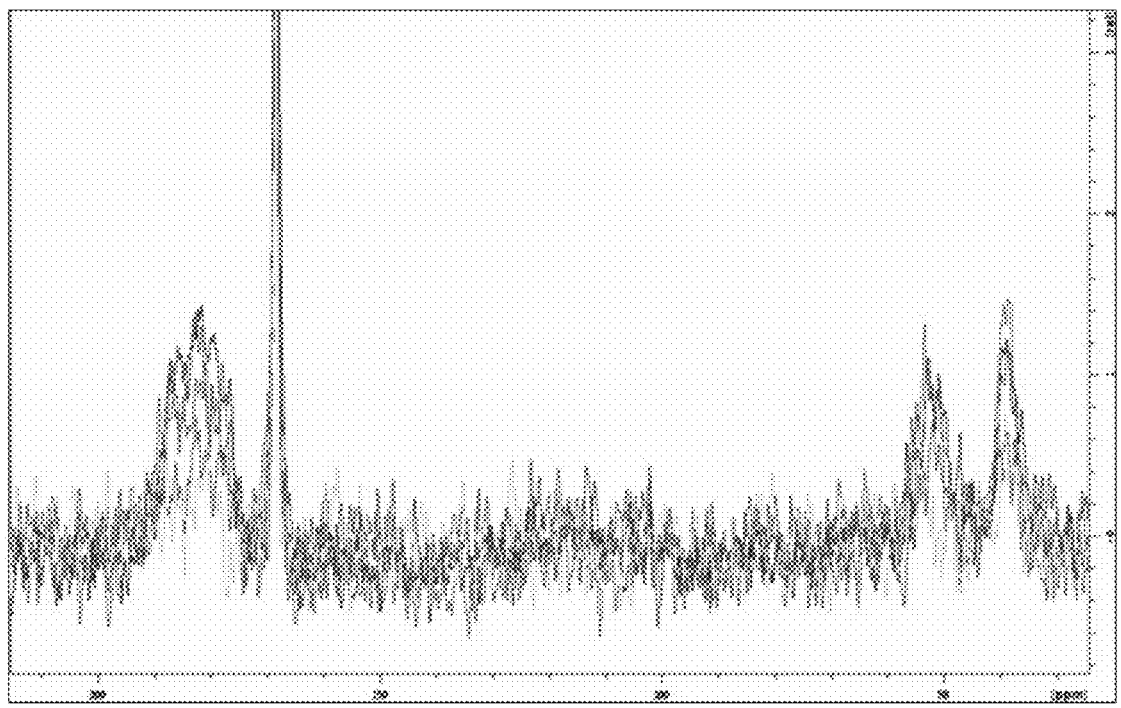
Figure 10B:
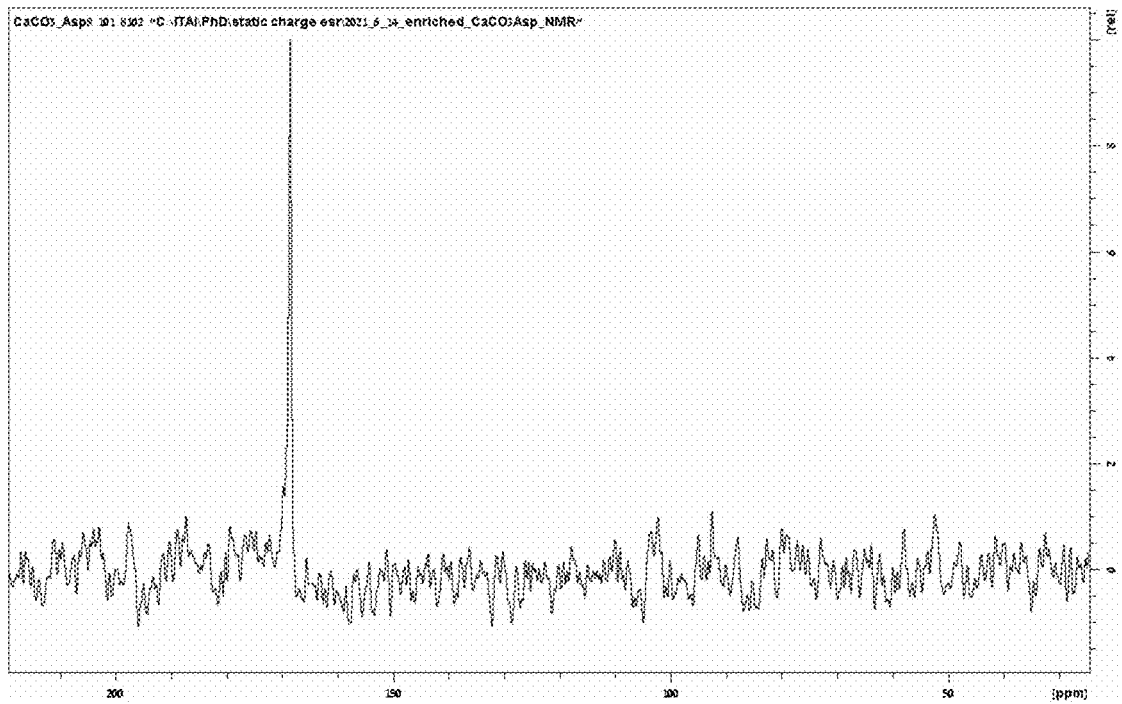

The $^{13}C$ NMR spectra obtained for Sample D are presented in FIGS. 9A and 9B. The $^{13}C$ NMR spectra for Sample E are shown in FIGS. 10A and 10B. The spectra lines colored blue, red, green, purple and yellow, in FIGS. 9A and 10A represent $\tau$ value of 0, 5, 10, 30, and 60 seconds respectively. Spectra shown in FIGS. 9B and 10B represent i value of 200 seconds. As can be seen for sample D, in FIG. 9A, the data at $\tau=0$ shows the signal of the $C\alpha$ and $C_\beta$ of the aspartic acid at ~52 ppm and ~38 ppm is suppressed to undetectable levels (owing to the CP supression). As more time is given for spin diffusion to take place, a resurgence of the aspartic acid peaks, already after merely one second of diffusion, is evident. With t values of a few seconds, a prominent signal that has diffused back from the matrix is observed. Also at a much longer i, of 200 sec, in FIG. 9B, a significant portion of the signal is seen. The polarization that remains intact after 200 sec amounts to ~30% of the polarization detected for $\tau=1$ sec, reflecting an effective T1 value on the order of 200 seconds!

For sample E, as shown in FIG. 10A, no resurgence of the signal occurs. In fact, whatever aspartic acid polarization that is detected is the result of incomplete polarization suppression carried out by the reversed CP step. The process revealed is of constant decay of the signal, just as would be expected from a neat material undergoing normal spin lattice relaxation. At $\tau=200$ sec in FIG. 10B, no polarization can be detected. the difference in behaviors for samples D and E articulated above demonstrate that the effective extension of the time window in which the polarization of the aspartic acid can be detected is indeed the result of polarization replenishment via spin diffusion from the matrix to the dopant.

Example 4—Spin Diffusion in a Hyperpolarized Model Sample

The rationale behind this example is to demonstrate that matrix/dopant formulation can be hyperpolarized and to demonstrate once again the mechanism of polarization retention by spin diffusion.

The sample used in this example was prepared in a way very similar to sample D, the only difference being that the concentration of aspartic acid in the precipitation solution was 3.5 mg/ml which is 10 fold higher than what was used in sample D and E. Measurement was conducted on a Bruker 400 DNP/MAS spectrometer at a temperature of 100K. Sample was wetted with a solution of TEKPOL radical 16 mM in tetrachloroethane, and polarization gained by DNP leaked into the particles via proton spin diffusion. The pulse sequence (CP Pump diffusion+DNP sequence) used in this example presented in FIG. 11 is very similar to what we used in Example 3, with the only difference being that there is no suppression block for the aspartic acid.

Figure 11:
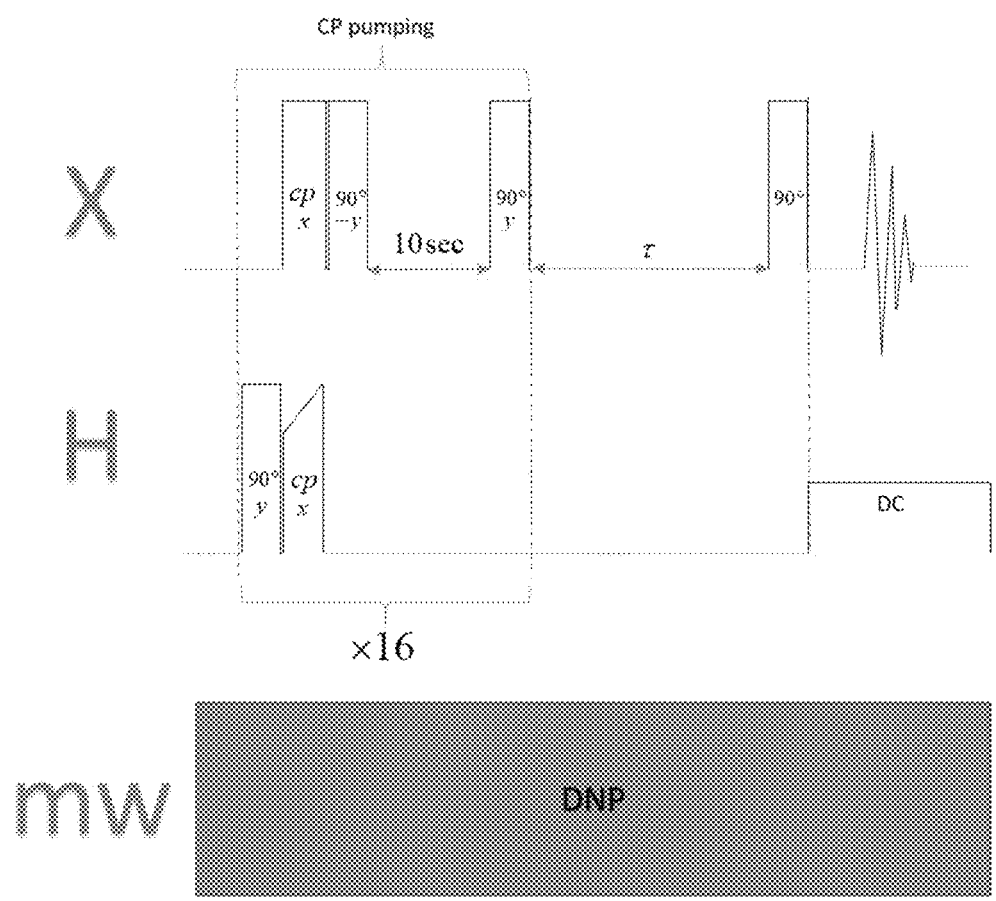
FIG. 11 depicts a diagram showing a polarization procedure performed to a matrix according to an embodiment.
Figure 12A:
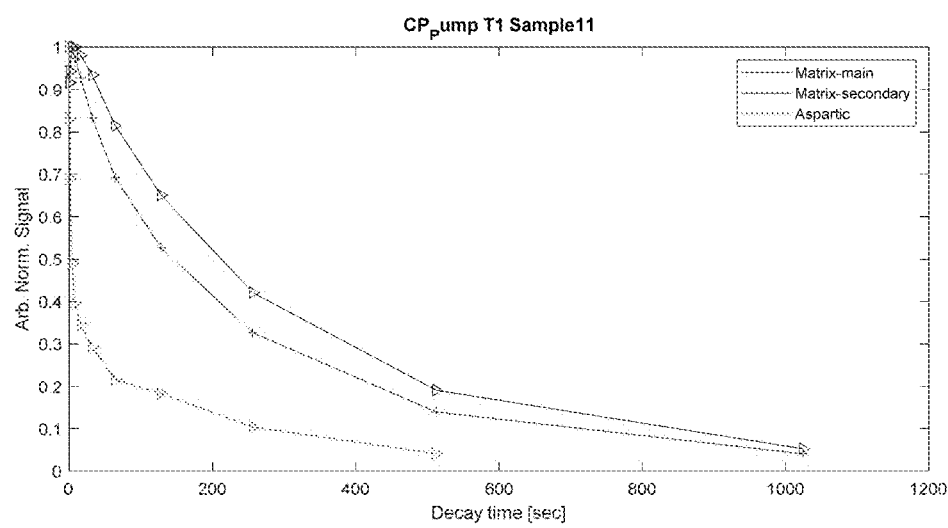
FIG. 12A depicts a graph showing decay time of signal intensity of a matrix and an aspartic acid dopant over time, in particles according to an embodiment.
Figure 12B:
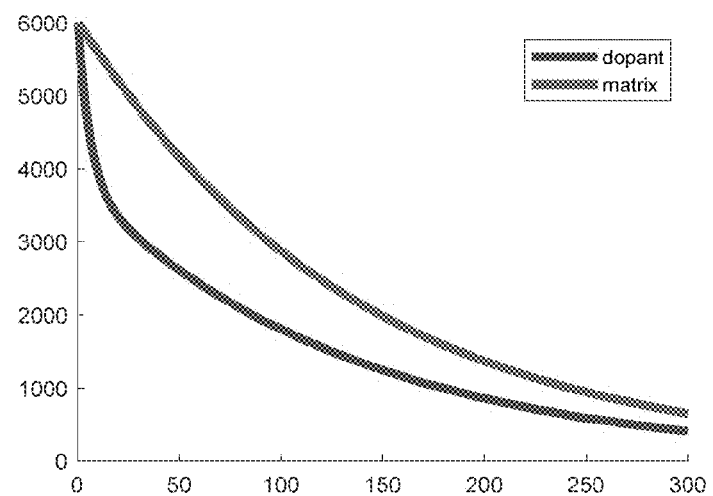
FIG. 12B depicts a graph showing decay in a simulation model of dopant and matrix.
Figure 12C:
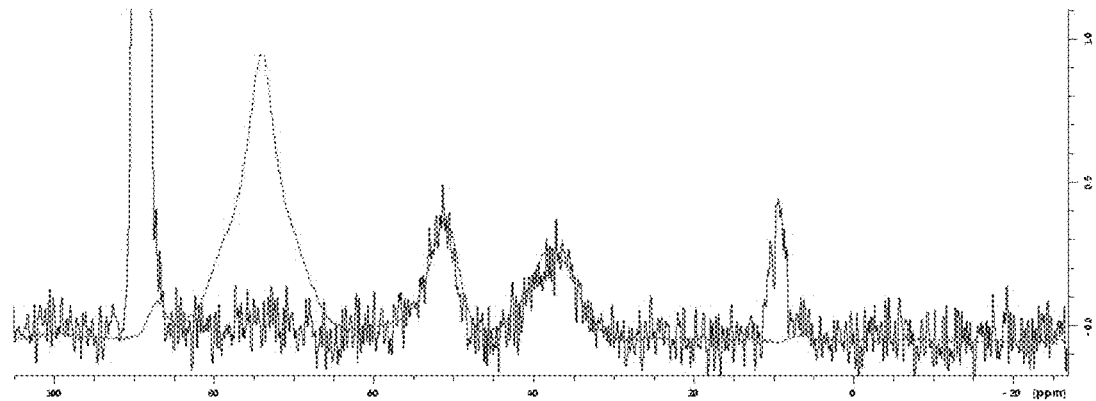
FIG. 12C depicts a comparison of signals of $^{13}C$ NMR spectra for a particle hyperpolarized (blue) and via direct excitation (red)

Using the pulse sequence of FIG. 11, a series of experiments with varying values of ti was conducted to assess the decay of the peaks of the aspartic acid. As can be seen in FIG. 12A, the decay is bi-phasic. In the first phase a fast decay owing both to residual spin diffusion and to intrinsic magnetization loss to relaxation is seen. Then, owing to the formation of a polarization gradient between the matrix and the aspartic acid, a slow decay phase in which spin diffusion from the matrix works to moderate magnetization decay in the aspartic acid. This very behavior is also seen in the numerical simulation shown in FIG. 12B. The correspondence between simulation and experiment constitutes strong support to the validity of the model. Next the extent to which the sample can be hyperpolarized was determined. To this end the signal acquired using the pulse sequence depicted in FIG. 11 with τ=0 was compared to the signal acquired using direct excitation with 2700 sec repetition delay as can be seen (not to scale) in FIG. 12C. The hyperpolarized signal is depicted in blue and direct excitation signal in red. The data reveals an enhancement factor of 40 with respect to the native signal available at room temperature, which is significant for DNP conducted at 100K. It is expected that optimization of hyperpolarization can lead to better results. The main conclusion that can be drawn from this is that hyperpolarization of matrix/dopant formulation is feasible.

Example 5—Preparation of Sample Comprising Calcium Carbonate Matrix Doped with Glycine In this example, a long relaxing matrix, calcium carbonate, is doped with a metabolite. Its preparation is done by adding glycine to two 200 mM solutions of sodium carbonate and calcium chloride, to result in a glycine concentration of 10 mg/ml in each solution. The solutions are set to be alkaline with pH=10-13. Next, one of the solutions is added to a 13 KDa dialysis bag. The bag is sealed and immersed in the other solution. After a few days, a precipitate forms and is collected. It is noted that the solutions may be prepared with heavy water or with water and heavy water at any ratio. The sample thus prepared is found to comprise predominantly of the calcite polymorph and contain up to 1.8% molar stoichiometric concentration of glycine with respect to matrix units.

Example 6: Preparation of Sample Comprising Glucose Matrix Doped with Pyruvic Acid In this example, the long relaxing matrix glucose is doped with a metabolite, pyruvic acid. The composition particles were prepared by dissolving glucose in water and placing the solution on hot plate to let most of the water evaporate. After most of the water evaporates and the solution assumes a very thick honey-like consistency, a solution of pyruvic acid in ethanol in an amount that will result in the desired concentration of pyruvic acid in the final product is added, given the concentration of the pyruvic acid in the ethanol solution. The solutions are then allowed to stir and homogenize. The vessel is then removed from heating and allowed to cool and crystalize. It is noted that the water used in this procedure may be regular water, heavy water or regular water and heavy water at any ratio.

Example 7—$T_1$ Extension for CaCO3/Glycine Matrix Dopant Formulation

In this example, a model system of calcium carbonate matrix doped with glycine was prepared. It was produced as described in U.S. Pat. No. 10,722,596. All steps in the preparation protocol we carried out using heavy water. A field of 300 Mhz was used at Room Temperature.

Figure 13:
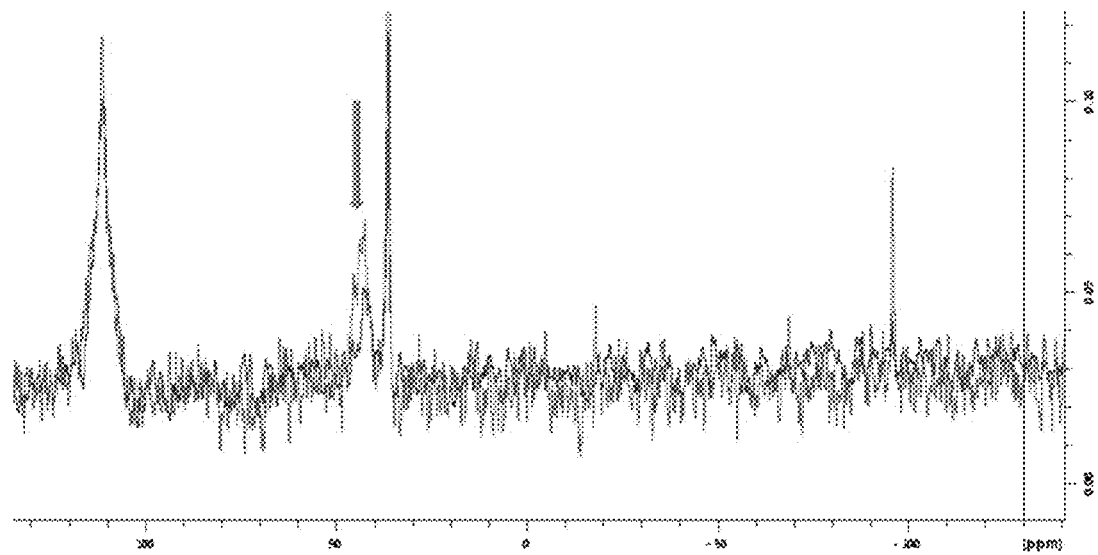
FIG. 13 depicts a $^{13}C$ NMR spectra of a particle comprising calcium carbonate matrix with glycine dopant at various repetition delays.

Using direct excitation only, the buildup of the glycine signal as a function of repetition delay was observed. The signal obtained at a repetition delay of 1000 seconds is larger by a factor of about 2 than the signal obtained with a repetition delay of 300 seconds. The data is presented in FIG. 13 and reflects a $T_1$ value of at least 390 sec. The arrow indicates the peak of interest. The upper red spectra line depicts a repetition delay of 1000 and the lower, blue spectra line depicts a repetition delay of 300.

The examples depicted herein show exemplary particles comprising matrix-dopant combinations which allow for hyperpolarization of dopants, thereby effectively providing longer $T_1$ times. Such particles may be useful for imaging of human patients.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

Described herein is a plurality of particles comprising a crystalline matrix and a dopant, wherein the matrix is present in an amount of between 80% and 99.99% of the plurality of particles by weight, and the matrix is a crystalline composition wherein one of the atoms of the matrix is a. $^{19}$F and $^{31}$P, or b. $^{13}$C, $^{15}$N, $^{29}$Si, $^{16}$, $^{17}$O, $^{23}$Na, $^{39}$K, $^{25}$Mg, $^{40}$Ca, $^{43}$Ca or deuterium; and the dopant is a compound involved in a biological process in a mammalian organism selected from the group consisting of: an amino acid, a monosaccharide, a disaccharide, a choline, a nucleobase, a carboxylic acid, or a biological waste product, a metabolite, a neurotransmitter, a peptide, a vitamin, a pharmaceutical agent, a hormone, a psychoactive agent, an alcohol, a glycol, glycerine, a fatty acid, a phospholipid, a lecithin, or cholesterol; and wherein the dopant is present in an amount of between 0.01% and 20% of the plurality of particles, and wherein when the matrix comprises an atom selected from the group of $^{13}$C, $^{15}$N, $^{29}$Si, $^{16}$O, $^{17}$O, $^{23}$Na, $^{39}$K, $^{25}$Mg, $^{40}$Ca, $^{43}$Ca and deuterium, and the dopant is isotopically enriched. Optionally, when the matrix comprises an atom selected from the group $^{19}$F and $^{31}$P, the dopant comprises the same atom, and when one of the atoms of the matrix is $^{13}$C, $^{15}$N, $^{29}$Si, $^{16}$O, $^{17}$O, $^{23}$Na, $^{39}$K, $^{25}$Mg, $^{40}$Ca, $^{43}$Ca, or deuterium, the dopant is isotopically enriched with the same atom. Optionally, the dopant is isotopically enriched with deuterium. Optionally, the matrix is isotopically enriched with deuterium. Optionally, the matrix and the dopant are each isotopically enriched with at least an atom selected from the group consisting of $^{13}$C, $^{15}$N, $^{29}$Si, $^{17}$O, or deuterium. Optionally, one of the atoms of the matrix and the dopant is $^{19}$F and $^{31}$P. Optionally, the matrix is a salt. Optionally, the salt comprises an ion selected from the group consisting of: $CO_3^{-2}$, $HCO_3^-$, $C_2O_4$, $PO_4$, $HPO_4$, $H_2PO_4$, $OH^-$, $NO_3$, and $NO_2$. Optionally, the salt is selected from the group consisting of: $CaCO_3$, $Na_2CO_3$, $K_2CO_3$, $NaHCO_3$, $KHCO_3$, $LiHCO_3$, $NH_4HCO_3$, $MgCO_3$, $CaC_2O_4$, $Na_2C_2O_4$, $K_2C_2O_4$, $Li_3PO_4$, $Na_3PO_4$, $K_3PO_4$, $(NH_4)_3PO_4$, $Ca_3(PO_4)_2$, $Mg_3(PO_4)_2$, $Ca(H_2PO_4)_2$, $CaHPO_4$, $Ca_5(PO_4)_3(OH)$, $Ca_{10}(PO_4)_6(OH)_2$, $Ca_{10}(PO_4)_6F_2$, $Ca_{10}(PO_4)_6C_{12}$, and $Ca_{10}(PO_4)_6Br_2$. Optionally, the salt is selected from the group consisting of: $CaCO_3$, $Na_2CO_3$, $K_2CO_3$, and $MgCO_3$ and wherein the carbonate ion and the dopant are isotopically enriched with $^{13}$C. Optionally, the matrix is a monosaccharide or disaccharide. Optionally, the matrix is glucose. Optionally, the amount of dopant is between 0.5% and 10% by weight. Optionally, the amount of dopant is between 1% and 10% by weight. Optionally, the dopant is an amino acid, or pyruvate. Optionally, the particles have a water solubility of between $1\times10^{-5}$ M and 6 M at room temperature. Optionally, the mean particle size is between 50 and 500 nanometers. Optionally, under ambient conditions and a magnetic field in the range of from 0.5 tesla (0.5 T) to 20 T, the matrix has a substantially long spin-lattice relaxation time ($T_1$), between 30 seconds to 1 hour. Optionally, the matrix and the dopant each contain an atom selected from the group consisting of $^{19}F$ and $^{31}P$, and wherein the dopant is deuterium enriched. Optionally, the dopant is uniformly dispersed within the particles. Optionally, the $T_1$ of the matrix is longer than the $T_1$ of the dopant at room temperature and at any magnetic field between 0.1 T and 20 T.

Further described herein is a method for preparing an imaging probe comprising, obtaining a plurality of particles according to claim 1 wherein the probe compound acts as the dopant, and polarizing the plurality of particles. Optionally, polarizing the plurality of compounds comprises hyperpolarization.

The invention claimed is:

1. A method for preparing an imaging probe comprising, obtaining a plurality of particles comprising a crystalline matrix and a dopant, wherein the matrix is present in an amount of between 80% and 99.99% of the plurality of particles by weight, and the matrix is a crystalline salt comprising an ion selected from the group consisting of: $CO_3^{-2}$, $HCO_3^-$, $C_2O_4$, $PO_4$, $HPO_4$, $H_2PO_4$, $OH^-$, $NO_3$, and $NO_2$ wherein at least one of the atoms of the matrix is selected from the group consisting of:
$^{13}C^{15}N$, $^{29}Si$, $^{16}O$, $^{17}O$, $^{23}Na$, $^{39}K$, $^{25}Mg$, $^{40}Ca$, $^{43}Ca$ and deuterium; and
the dopant is isotopically enriched with the same atom, and the dopant is a compound involved in a biological process in a mammalian organism selected from the group consisting of: an amino acid, a monosaccharide, a disaccharide, a choline, a nucleobase, a carboxylic acid, or a biological waste product, a metabolite, a neurotransmitter, a peptide, a vitamin, a pharmaceutical agent, a hormone, a psychoactive agent, an alcohol, a glycol, glycerine, a fatty acid, a phospholipid, a lecithin, or cholesterol; and wherein the dopant is present in an amount of between 0.01% and 20% of the plurality of particles by weight, and the dopant acts as the imaging probe;
wherein the particles have a water solubility of between $1 \times 10^{-5}$ M and 6 M at room temperature; and wherein the dopant is uniformly dispersed within the particles; and polarizing the plurality of particles.

2. The method according to claim 1, wherein polarizing the plurality of compounds comprises hyperpolarization.

3. The method according to claim 1, wherein the matrix and the dopant are each isotopically enriched with at least an atom selected from the group consisting of: $^{13}C$, $^{15}N$, $^{29}Si$, $^{17}O$, or deuterium.

4. The method according to claim 1 wherein the salt is selected from the group consisting of: $CaCO_3$, $Na_2CO_3$, $K_2CO_3$, $NaHCO_3$, $KHCO_3$, $LiHCO_3$, $NH_4HCO_3$, $MgCO_3$, $CaC_2O_4$, $Na_2C_2O_4$, $K_2C_2O_4$, $Li_3PO_4$, $Na_3PO_4$, $K_3PO_4$, $(NH_4)_3PO_4$, $Ca_3(PO_4)_2$, $Mg_3(PO_4)_2$, $Ca(H_2PO_4)_2$, $CaHPO_4$, $Ca_5(PO_4)_3(OH)$, $Ca_{10}(PO_4)_6(OH)_2$, $Ca_{10}(PO_4)_6F_2$, $Ca_{10}(PO_4)_6C_{12}$, and $Ca_{10}(PO_4)_6Br_2$.

5. The method according to claim 4 wherein the salt is selected from the group consisting of: $CaCO_3$, $Na_2CO_3$, $K_2CO_3$, and $MgCO_3$ and wherein the carbonate ion and the dopant are isotopically enriched with $^{13}C$.

6. The method according to claim 1, wherein the amount of dopant is between 0.5% and 10% by weight.

7. The method according to claim 6, wherein the amount of dopant is between 1% and 10% by weight.

8. The method according to claim 1 wherein the dopant is an amino acid, or pyruvate.

9. The method according to claim 1 wherein, the mean particle size is between 50 and 500 nanometers.

10. The method according to claim 1 wherein under ambient conditions and a magnetic field in the range of from 0.5 tesla (0.5 T) to 20 T, the matrix has a substantially long spin-lattice relaxation time ($T_1$), between 30 seconds to 1 hour.

11. The method according to claim 8 wherein the dopant is glycine.

12. The method according to claim 1 wherein upon polarization, magnetization is conducted from the matrix to the dopant.

13. The method according to claim 1, further comprising administering the imaging probe to a patient in need thereof, and performing an imaging procedure on the patient.

14. The method according to claim 13, wherein the imaging procedure is magnetic resonance imaging.

* * * * *